(12) United States Patent
Rudolph et al.

(10) Patent No.: US 8,598,228 B2
(45) Date of Patent: Dec. 3, 2013

(54) CINNAMIC ACID ASCORBATES

(75) Inventors: Thomas Rudolph, Darmstadt (DE); Philipp Buehle, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 13/319,407

(22) PCT Filed: Apr. 12, 2010

(86) PCT No.: PCT/EP2010/002242
§ 371 (c)(1), (2), (4) Date: Nov. 8, 2011

(87) PCT Pub. No.: WO2010/127756
PCT Pub. Date: Nov. 11, 2010

(65) Prior Publication Data
US 2012/0052028 A1    Mar. 1, 2012

(30) Foreign Application Priority Data
May 8, 2009 (EP) .................................... 09006272

(51) Int. Cl.
*A61K 31/34* (2006.01)
*A61Q 17/04* (2006.01)
*C07D 307/62* (2006.01)

(52) U.S. Cl.
USPC .............................. 514/474; 424/59; 549/315

(58) Field of Classification Search
USPC ........................ 424/59, 62; 514/474; 549/315
See application file for complete search history.

(56) References Cited

U.S. PATENT DOCUMENTS

| 5,536,500 | A | 7/1996 | Galey et al. |
| 6,238,650 | B1 | 5/2001 | Lapidot et al. |
| 6,242,099 | B1 | 6/2001 | Grandmontagne et al. |
| 7,354,893 | B2 | 4/2008 | Dilk |
| 7,863,478 | B2 | 1/2011 | Carola et al. |
| 2004/0220137 | A1 | 11/2004 | Sauermann |
| 2007/0014822 | A1 | 1/2007 | Dilk |
| 2008/0038213 | A1 | 2/2008 | Carola et al. |
| 2010/0167936 | A1 | 7/2010 | Rudolph et al. |
| 2010/0322881 | A1 | 12/2010 | Rudolph et al. |

FOREIGN PATENT DOCUMENTS

| DE | 101 33 202 A1 | 1/2003 |
| DE | 10 2006 037 724 A1 | 2/2008 |
| EP | 0 487 404 A1 | 5/1992 |
| EP | 0 664 290 A1 | 7/1995 |
| EP | 1 939 192 A1 | 7/2008 |
| JP | 2009-35509 A | 2/2009 |
| WO | 93/04665 A1 | 3/1993 |
| WO | 00/09652 A2 | 2/2000 |
| WO | 00/71084 A1 | 11/2000 |
| WO | 00/72806 A2 | 12/2000 |
| WO | 2006/018104 A1 | 2/2006 |
| WO | 2008/017346 A2 | 2/2008 |
| WO | 2009/097953 A1 | 8/2009 |
| WO | 2010/060513 A2 | 6/2010 |

OTHER PUBLICATIONS

Schlossman, M., "Treated Pigments—New Ways to Impart Color on the Skin," Cosmetics & Toiletries, Feb. 1990, vol. 105, pp. 53-64.
Lemanska, K., et al., "Effect of Substitution Pattern on TEAC Antioxidant Activity of Mono- and Dihydroxyflavones," Current Topics in Biophysics, 2000, 24(2), pp. 101-108.
Rice-Evans, C.A., et al., "Antioxidant properties of phenolic compounds," Trends in Plant Science, Apr. 1997, vol. 2, No. 4, pp. 152-159, Elsevier Science Ltd.
Lemanska, K., et al., "The Influence of pH on Antioxidant Properties and the Mechanism of Antioxidant Action of Hydroxyflavones," Free Radical Biology & Medicine, 2001, vol. 31, No. 7, pp. 869-881, Elsevier Science Inc.
International Search Report, dated Aug. 9, 2010, issued in corresponding PCT/EP2010/002242.

*Primary Examiner* — Noble Jarrell
*Assistant Examiner* — John S Kenyon
(74) *Attorney, Agent, or Firm* — Millen, White, Zelano & Branigan, P.C.

(57) ABSTRACT

The invention relates to specific cinnamic acid ascorbates and to the use thereof as UV filters which bond to the skin, and to a process for the preparation thereof, and to preparations comprising these compounds.

14 Claims, No Drawings

CINNAMIC ACID ASCORBATES

The invention relates to specific cinnamic acid ascorbates and to the use thereof as UV filters which bond to the skin, and to a process for the preparation thereof, and to preparations comprising these compounds.

The human skin undergoes certain ageing processes, some of which are attributable to intrinsic processes (chronoageing) and some of which are attributable to exogenous factors (environmental, for example photoageing).

The exogenous factors include, in particular, sunlight or artificial radiation sources having a comparable spectrum, and compounds which are able to form due to the radiation, such as undefined reactive photoproducts, which may also be free radicals or ionic.

A multiplicity of organic and inorganic UV filters and antioxidants which are able to absorb UV radiation and scavenge free radicals is known. They are thus able to protect the human skin. These compounds catalyse the trans-formation of UV light into heat.

Owing to poor skin adhesion, however, the duration of protection is limited, in particular since conventional UV filters can be washed off very easily, for example by sweat or water.

It is a known strategy, for example from WO 2006/018104, to derivatise UV filters or self-tanning substances in such a way that they can covalently bond to the stratum corneum of the epidermis via a reactive moiety and thus functionalise the skin with the UV filter or self-tanning agent. For effective bonding to proteins and amino acids in the outer layers of the skin, it is necessary for the corresponding UV filter derivatives, or derivatives of other active compounds, such as pharmacological, antimicrobial, fungicidal, herbicidal, insecticidal or cosmetic active compounds, X-ray contrast agents or dyes, to have the highest possible reactivity of their bonding-capable moieties.

WO 2008/017346 discloses, for example, ascorbic acid derivatives which can be used as UV filters which bond to the skin.

However, there continues to be a demand for skin-tolerated compounds for UV protection, in particular based on cinnamic acid, which are capable of functionalising protein-containing matrices or in other words are capable of associating and optionally forming covalent bonds with substances which contain free NH, $NH_2$, SH or OH groups, can be incorporated in a suitable manner into cosmetic or pharmacological preparations and, in particular, are more stable, both with respect to reversible photoreactions and also with respect to irreversible photoreactions, than UV filters known to date whose structure is based on cinnamic acid.

The object of the invention was correspondingly to find alternative skin-tolerated compounds which are able to meet this demand.

Surprisingly, it has now been found that specific cinnamic acid ascorbates of the formula I achieve this object to a particular extent. In accordance with the invention, both D- and L-ascorbic acid or mixtures thereof can be derivatised to give compounds of the formula I.

The invention therefore relates firstly to compounds of the formula I,

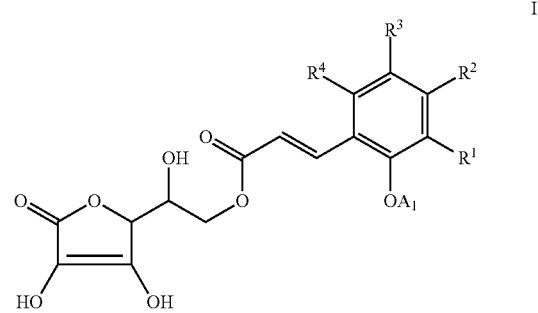

where $A_1$ stands for H or a straight-chain or branched alkyl group having 1 to 20 C atoms, $R^1$ to $R^4$ each stand, independently of one another, for H, straight-chain or branched alkoxy groups having 1 to 20 C atoms, hydroxyl, fluorinated straight-chain or branched alkoxy groups having 1 to 20 C atoms or alkyl-carbonyloxy, and alkylcarbonyloxy stands for alkyl-C(=O)—O, where alkyl denotes a straight-chain or branched alkyl group having 1 to 10 C atoms.

In accordance with the invention, it is also possible to employ derivatives of the compounds of the formula I, which may be in substituted form in the 2- and/or 3-position on the ascorbic acid moiety. By means of suitable measures, these protected hydroxyl groups of the compounds of the formula I can be deprotected after application to the skin and are thus available for bonding to the skin. Examples of modified hydroxyl groups in the 2- and/or 3-position on the ascorbic acid moiety of the compounds of the formula I are —O-alkyl, —OC(O)-alkyl, —$OPO_3M$ or O-glycosyl, where alkyl denotes a straight-chain or branched alkyl group having 1 to 20 C atoms, and M denotes an alkali metal cation, alkaline-earth metal cation or H.

The bonding of a carbohydrate in position 2 or 3 of the ascorbic acid, referred to as O-glycosyl above, can take place, for example, for monosaccharides, such as ribose, arabinose, xylose, lyxose, allose, altrose, glucose, mannose, gulose, idose, galactose, talose, ribulose, xylulose, psicose, fructose, sorbose or tagatose. This list includes both isomers, i.e. in each case the D or L forms.

Preference is given to the use of glucose, galactose or fructose, very particularly preferably glucose.

In principle, however, disaccharides, such as saccharose (or also known as sucrose), lactose, trehalose, maltose, cellobiose, gentiobiose or melibiose, are also suitable. This list includes both the α and also the β forms.

From the group of the disaccharides, preference is given to the use of saccharose or lactose, particularly preferably saccharose.

EP 664290 discloses similar cinnamic acid ascorbates, for example dicinnamoyl 2O,6O-ascorbate. These compounds can be synthesised, inter alia, via monocinnamoyl 6-O-ascorbates, which are described by the general structural formula

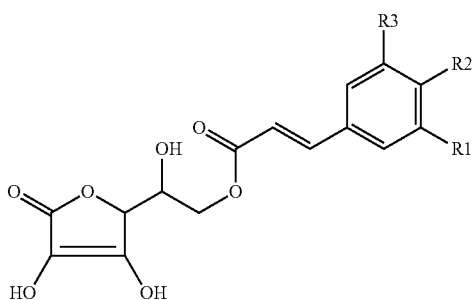

where R1 to R3 can denote, independently of one another, H, alkoxy, hydroxyl, alkylcarbonyloxy or fluoroalkoxy. However, EP 664290 does not discloses any example of a monocinnamoyl 6-O-ascorbate of this type.

JP 2009-035509 describes the enzymatic synthesis of monocinnamoyl 6-O-ascorbates of the structure

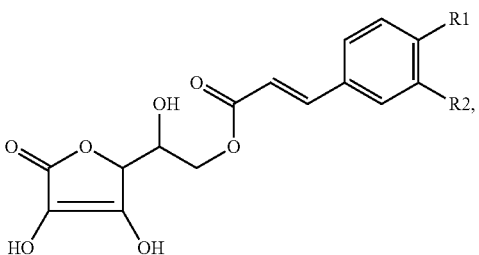

where R1 and R2 can denote, independently of one another, H, hydroxyl or lower alkoxy.

WO 2008/017346 likewise describes similar monocinnamoyl 6-O-ascorbates of a broad general formula, but where 4-methoxycinnamoyl 6-O-ascorbate is disclosed as an individual compound.

The compounds of the formula I according to the invention differ in principle from all monocinnamoyl 6-O-ascorbates known to date through the substituent $OA_1$ in the ortho-position, which is, in particular, responsible for the advantages of the compounds according to the invention.

The substances of the formula I according to the invention exhibit, in particular, advantages over the known cinnamic acid derivatives with respect to reversible photoreactions.

For known cinnamic acid derivatives, trans,cis-photoisomerisation, for example, is known as a reversible photoreaction. The thermodynamically more stable trans isomer can be set in so-called photostationary equilibrium with the cis isomer (=photoisomer) by means of UV light.

Thus, the light-protection expert knows, for example, that the cosmetic UV filter ethylhexyl methoxycinnamate EHMC (e.g. Eusolex® 2292), which is used worldwide, is in the form of the pure trans isomer in its synthesis form. By UV irradiation in solution or in the cosmetic, a photostationary equilibrium is established, depending on the matrix circumstances and spectral characteristics of the UV source, in which the proportion of the trans isomer is generally now 40-60%. In parallel, 60-40% of the cis isomer (=photo-isomer) are formed. This situation can also be expected for the monocinnamoyl 6-O-ascorbates from the prior art and has been confirmed in a representative manner and is described in Examples 5 and 6 for the example of 3,4-dimethoxycinnamoyl 6-O-ascorbate (S)-2-((R)-3,4-dihydroxy-5-oxo-2,5-dihydrofuran-2-yl)-2-hydroxyethyl (3-(3,4-dimethoxyphenyl)acrylate).

It is characteristic of cis photoisomers that their absorptive power is reduced compared with the trans isomer. For cis-EHMC, the specific absorbance at the absorbance maximum is greatly reduced ($\epsilon=13,500$, $\lambda max(MeOH)[nm]=304$). By contrast, the specific absorbance of trans-EHMC is significantly higher ($\epsilon=24,550$, $\lambda max(MeOH)[nm]=309$). [See in this respect: M. Köhnlein: "Untersuchungen zum photochemischen Verhalten des UVB-Filters Octyl-methoxycinnamat in Modellsystemen, Sonnenschutzmitteln sowie auf der Haut" [Investigations of the Photochemical Behaviour of the UVB Filter Octyl Methoxycinnamate in Model Systems, Sunscreens and on the Skin]; Thesis, University of Hohenheim 2000; ISBN 3-8265-8234-9].

It is therefore desirable for the cosmetic chemist for as little photoisomer as possible to form, since its specific absorptive capacity is greatly reduced compared with the trans isomer, and the integral absorptive power of the two isomers is thus weakened under irradiation conditions.

The substances of the formula I according to the invention have greatly improved photobehaviour with respect to the reversible photoreaction, which gives rise to considerable advantages of the compounds according to the invention with respect to the stability in preparations for practical use in UV protection.

In the compounds of the formula I, the straight-chain or branched alkyl group having 1 to 20 C atoms denotes, for example, methyl, ethyl, propyl, n-butyl, tert-butyl, n-pentyl, n-hexyl, 2-ethylhexyl, n-dodecyl or n-lauryl. A straight chain or branched alkyl group having 1 to 4 C atoms is preferably used.

In the compounds of the formula I, the straight-chain or branched alkoxy group having 1 to 20 C atoms denotes, for example, methoxy, ethoxy, propoxy, isopropoxy, butoxy, isobutoxy, tert-butoxy, n-pentoxy, n-hexyloxy, n-heptyloxy, n-octyloxy, n-ethylhexyloxy, n-dodecyloxy or n-lauryloxy. The alkoxy group preferably has 1 to 6 C atoms, particularly preferably 1 to 4 C atoms. The alkoxy group is very particularly preferably methoxy.

Fluorinated straight-chain or branched alkoxy groups correspond to the alkoxy groups just described with some or all of the H atoms replaced by F, for example trifluoromethoxy, pentafluoroethoxy, trifluoromethylethoxy, heptafluoropropoxy or nonafluorobutoxy.

$A_1$ in formula I preferably denotes a straight-chain or branched alkyl group having 1 to 20 C atoms, particularly preferably a straight-chain or branched alkyl group having 1 to 4 C atoms, very particularly preferably methyl.

$R^2$ in formula I preferably denotes H, hydroxyl or a straight-chain or branched alkoxy group having 1 to 20 C atoms. $R^2$ is particularly preferably hydroxyl or a straight-chain or branched alkoxy group having 1 to 4 C atoms. $R^2$ is very particularly preferably an alkoxy group having 1 to 4 C atoms.

$R^1$, $R^3$ and $R^4$ are each, independently of one another, preferably H, hydroxyl or a straight-chain or branched alkoxy group having 1 to 20 C atoms.

In a preferred embodiment of the compounds of the formula I, at least one further substituent selected from $R^1$, $R^3$ or $R^4$ denotes hydroxyl or a straight-chain or branched alkoxy group having 1 to 20 C atoms, preferably a straight-chain or branched alkoxy group having 1 to 4 C atoms.

Overall, it is preferred for at least two straight-chain or branched alkoxy groups having C atoms as described above to be present on the benzene ring. It is particularly preferred for three straight-chain or branched alkoxy groups having C atoms as described above to be present on the benzene ring.

Particularly preferred compounds of the formula I are
2,4-dimethoxycinnamoyl 6-O-ascorbate,
2,4,6-trimethoxycinnamoyl 6-O-ascorbate,
2,3,4-trimethoxycinnamoyl 6-O-ascorbate,
2,4,5-trimethoxycinnamoyl 6-O-ascorbate.

In contrast to the known cinnamic acid derivative 4-methoxycinnamoyl 6-O-ascorbate, whose UV absorption is in the UVB region (by definition, the UV absorption maximum is between 290 nm and 320 nm), it is preferred for UV filters according to the invention to absorb to a greater extent in the UVA region. In the ideal case, the UV absorption maximum is in the range between 320 nm and 400 nm. The compounds of the formula I according to the invention, or the compounds as described above which are described as preferred, are, in particular, UVA filters which bond to the skin and/or bond to the hair.

The invention therefore furthermore also relates to the use of the compounds of the formula I according to the invention, as described above, as UV filters which bond to the skin, in particular as UVA filters which bond to the skin.

The compounds of the formula I can generally be prepared by esterification.

The invention therefore furthermore relates to a process for the preparation of the compounds of the formula I according to the invention, as described above, characterised in that ascorbic acid is esterified using a compound of the formula II,

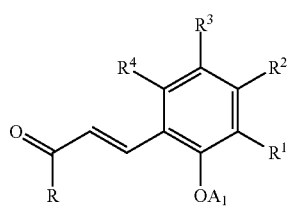

II where R denotes OH, halogen or an active ester, halogen denotes Cl, Br or I, and the substituents $A_1$, $R^1$ to $R^4$ have a meaning defined above.

Ascorbic acid is commercially available. The compounds of the formula II are in some cases commercially available or can be synthesised by methods which are described, for example, in the standard works, such as Houben-Weyl, Methoden der organischen Chemie [Methods of Organic Chemistry], Georg-Thieme-Verlag, Stuttgart, to be precise under reaction conditions which are known and suitable for the said reactions. Use can also be made here of variants known per se, which are not mentioned in greater detail here.

The direct esterification of the compounds of the formula II using ascorbic acid, where R=OH in formula II, is carried out, for example, in the presence of concentrated sulfuric acid and preferably under inert-gas conditions. The mixture of the components is advantageously prepared at temperatures <5° C. The actual reaction temperature is between 10 and 60° C., preferably between 15 and 30° C. The reaction is particularly preferably carried out at room temperature.

Instead of the free acid of the formula II, as defined above for R=OH, it is also possible to employ derivatives of the formula II, preferably a pre-activated acid or an acid halide (R=halogen, preferably Cl), a symmetrical or mixed anhydride or an active ester. Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart). Activated esters are advantageously formed in situ from compounds of the formula I where R=OH, for example by addition of HOBt (1-hydroxybenzotriazole) or N-hydroxysuccinimide.

The reaction is generally carried out in an inert solvent, on use of a halide of the formula II in the presence of an acid-binding agent, preferably an organic base, such as triethylamine, dimethylaniline, pyridine, dimethyl-aminopyridine or quinoline.

The addition of an alkali or alkaline-earth metal hydroxide, carbonate or bicarbonate or of another salt of a weak acid of the alkali or alkaline-earth metals, preferably of potassium, sodium, calcium or caesium, may also be favourable.

Enzymatic esterifications, for example by lipases, are also suitable.

Owing to the synthesis, the direct esterification gives rise to a mixture of ascorbic acid C-6 esters and ascorbic acid C-5 esters, where the ascorbic acid C-6 ester generally predominates, i.e. compounds of the formula I. These mixtures can also be incorporated directly into the preparations according to the invention. These mixtures can of course be separated by methods which are known to the person skilled in the art, enabling the pure compounds of the formula I to be isolated. Depending on the proportion of the corresponding ascorbic acid C-5-ester, isolation is, however, not necessary for the application according to the invention.

The free hydroxyl groups in the 2- and 3-position of ascorbic acid can optionally also be blocked using protecting groups before the actual esterification, if this appears necessary.

The ascorbic acid C-5-esters of the compounds of the formula I can be prepared through the following formula I-1:

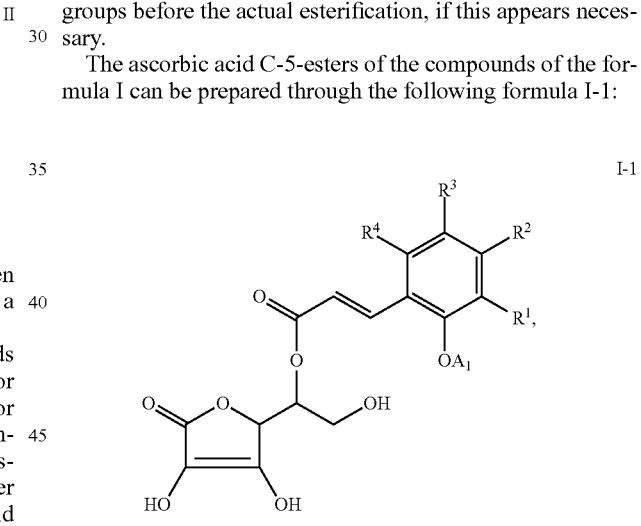

I-1 where the substituents $A_1$, $R^1$ to $R^4$ have one of the meanings given above. The same comments regarding possible substituents and degradation products as described for the compounds of the formula I apply to the compounds of the formula I-1.

For the bonding of substances according to the invention to proteins or protein- or amino acid-containing matrices, such as the stratum corneum of the skin, it is advantageous for the ascorbic acid moiety to undergo a degradation reaction comparable to the ascorbic acid Maillard reaction. This degradation is characterised by typical, optionally successive reactions. Typical reactions of this type to which the starting substance can accordingly be subjected can include, for example, dehydrogenation, dehydration, hydration, hydrolysis, oxidation, isomerisation and/or elimination (for example of water and/or carbon dioxide). In particular, oxidation to corresponding dehydroascorbates can be assumed to be the initial step here.

Illustrative structures which can be postulated via Maillard reaction-analogous mechanisms (primary Maillard products) are listed below. Illustrative structures can be regarded as intermediates which are able to bond to proteins of the stratum corneum.

The formation of the illustrative structures shown can at the same time be regarded as activation of the starting substances, since this can increase the chemical reactivity with respect to the reaction with proteins.

Accordingly, it may be the aim, depending on the application, to allow these structures to form specifically from the starting substance by chemical reaction in order to achieve an increased protein-bonding reaction. The degradation reaction here is preferably initiated by oxidation. Oxidation can be initiated by exposure to oxygen/air or can also take place, for example, by photooxidation in the presence of suitable radiation, such as, for example, UV light or sunlight. However, oxidation can also be caused by the specific use of oxidants. Suitable oxidants by way of example are, for example, peroxides, such as hydrogen peroxide or hydroperoxides, ozone, free radicals, reactive oxygen species or inorganic oxidants, such as iron(III)/(II) or copper(II)/(I) salts.

The said activation by oxidants can be achieved, for example, by mixing a preparation comprising the oxidant and a second preparation comprising the starting substance with one another immediately before application to skin or hair or, for example, treating the skin at a different time firstly with the second preparation comprising the starting substance and subsequently applying the first preparation comprising the oxidant.

Oxidation reactions by atmospheric oxygen after application occur with high conversion if the application layer is applied as thinly as possible. However, the preparation or the solvent in which substances according to the invention are applied also has a high influence here. In particular, polar-protic solvents, such as water, glycols and glycol derivatives (e.g. glycerol, ethyl-ene glycol, polyethylene glycols), promote bonding to the skin. In addition, it may be helpful to render the substance environment alkaline after application in order to accelerate the bonding to the skin. In addition, it is conceivable to render either the application area or the preparation comprising the starting substance alkaline by addition of a further preparation even before application of the starting substance. The expression "render alkaline" is generally taken to mean increasing the ambient pH of the ascorbic acid derivative in the preparation, which is generally as low as possible, application-specifically on an ad hoc basis in order specifically to increase its oxidation sensitivity and the associated protein-bonding ability (e.g. by treatment with NaOH or other chemical bases).

So-called primary Maillard products as shown in the table can, like the starting substances, be regarded as individual UV filters which bond to the skin and hair and can be combined with the starting substances, i.e., for example, the compounds of the formula I or cis isomers thereof or 5-O-ascorbates thereof.

Table: Early Maillard Products of Monocinnamoyl Ascorbates Having Protein-Bonding Ability which can be Postulated by Way of Example

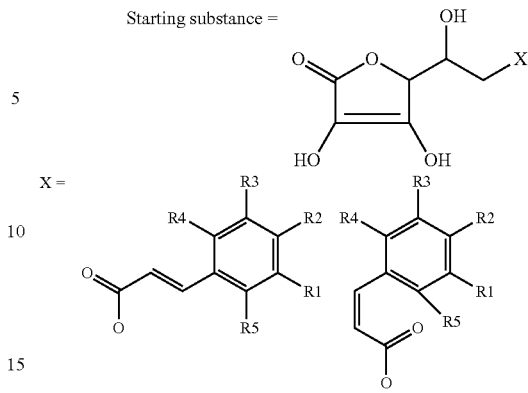

where R1-R5 represent, independently of one another, H, alkoxy, hydroxyl, alkylcarbonyloxy or fluoroalkoxy, as described above, and, for the starting substances according to the invention, $R5=OA_1$, as described above. The above description likewise applies correspondingly to the definitions of the substituents R1 to R5.

Illustrative primary Maillard products:

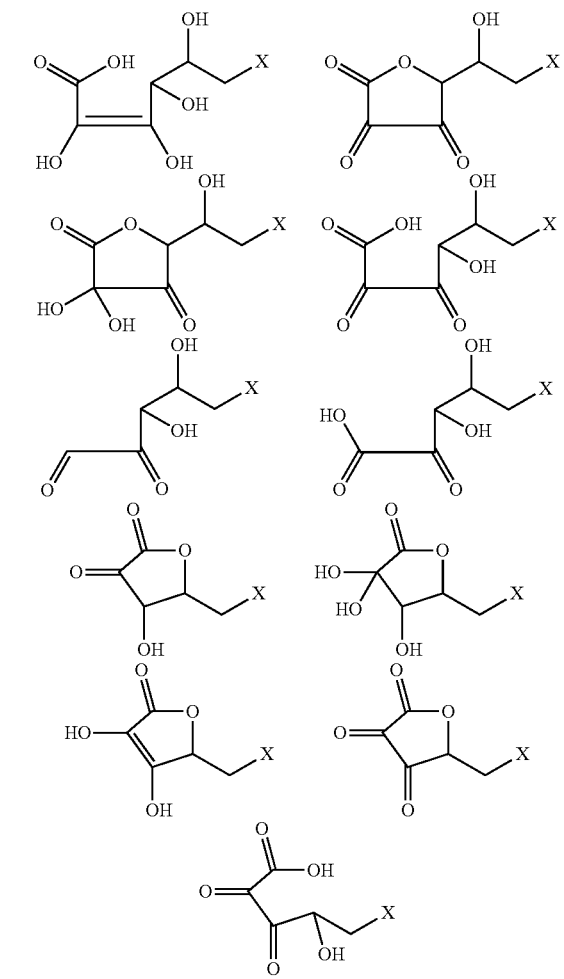

The primary degradation products of the starting substances, which are shown here by way of example, can undergo further chemical changes before reacting with the proteins, e.g. of skin and hair. These changes can be described by way of example as dehydrogenation, dehydration, hydrolysis, oxidation, isomerisation, hydration and/or elimination (e.g. of water and/or carbon dioxide). Analogous considerations can be applied to the corresponding isomeric ascorbic acid 5O-esters.

The substances of the formula I according to the invention, and, for example, also 4-methoxycinnamoyl 6-O-ascorbate, are also distinguished, besides their high skin-bonding capacity, additionally by the fact that they are readily biodegradable in the environment.

Further advantages of substances according to the invention, and, for example, also of 4-methoxycinnamoyl 6-O-ascorbate, can be seen in their antimicrobial efficacy. Furthermore, these substances are suitable for improving the skin barrier. They may have a wound-healing action, and possibly act against cellulite and the various forms of acne. Their anti-ageing action is attributable not only to their UV-filtering action, but also goes back to modes of action as described above for ascorbic acid. Besides the inhibition of so-called matrix metalloproteinases (additional anti-ageing effect), the substances described may also influence skin colour or hair colour. In particular in combination with classical self-tanning substances, such as dihydroxyacetone or erythrulose (but also in the absence thereof), desired effects, such as tanning intensification, tanning prolongation, or an increase in the red content in the tanning picture, can be achieved. Since the skin-lightening action of ascorbic acid is known, a skin-lightening action can also be achieved with the substances described here, optionally in synergistic combination with known skin-lightening agents.

Owing to their antioxidative properties, the substances of the formula I according to the invention are eminently suitable as product protection components for preventing oxidative degradation of sensitive recipe constituents in preparations, such as dyes, perfume components or vitamins.

They may be associated with the fragrances described by way of example below or stabilise the latter:

All fragrances as described in "S. Arctander, Perfume and Flavor Materials, Vol. I and II, Montclair, N.J., 1969, Selbstverlag" or in "K. Bauer, D. Garbe and H. Surburg, Common Fragrance and Flavor Materials, 4th Ed., Wiley-VCH, Weinheim 2001". All fragrances as described in U.S. Pat. No. 7,354,893 B2.

The invention therefore furthermore also relates to the use of compounds of the formula I, as described above, for product protection of sensitive preparation constituents.

Substances according to the invention can be provided as a particulate administration form. The average particle sizes here can be 0.001-0.1 µm, preferably 0.1-5 µm. A distribution having a d50 value (laser diffraction) of 100 nm-1 µm is particularly preferred. The active compounds can be provided alone or mixed with carrier materials, such as, for example, sorbitol or mannitol. In this administration form, the substances can develop a depot action on topical application and release the active compound to the skin little by little. This takes place by means of the follicular, transcellular or intercellular (corneocyte) penetration route. The substances according to the invention can furthermore be provided in the form of oily mixtures with typical oils/emollients from the pharmaceutical or cosmetic industry. Dispersion assistants are used in this case.

The present invention furthermore relates to preparations which comprise at least one compound of the formula I with the compounds of the formula I described above or indicated as preferred or the individual compounds listed.

The preparations here are usually preparations which can be applied topically, for example cosmetic or dermatological formulations or medical products. In this case, the preparations comprise a cosmetically or dermatologically suitable carrier and, depending on the desired property profile, optionally further suitable ingredients. In the case of pharmaceutical preparations, the preparations in this case comprise a pharmaceutically tolerated carrier and optionally further pharmaceutical active compounds.

"Can be applied topically" in the sense of the invention means that the preparation is applied externally and locally, i.e. that the preparation must be suitable for, for example, application to the skin.

Preferred preparations are cosmetic preparations.

In the sense of the present invention, the term composition or formulation is also used synonymously besides the term preparation.

The preparations may include or comprise, essentially consist of or consist of the said requisite or optional constituents. All compounds or components which can be used in the preparations are either known and commercially available or can be synthesised by known processes.

Further preferred combinations of embodiments are disclosed in the Claims.

The invention also relates to a process for the preparation of a preparation, as described above, in which at least one compound of the formula I is mixed with a carrier and optionally with further active compounds or assistants. Suitable carrier substances and active compounds or assistants are described in detail in the following part.

In preferred embodiments, the at least one compound of the formula I having the substituents which are defined or indicated as preferred or preferred individual compounds are typically employed in the preparations according to the invention in amounts of 0.05 to 10% by weight, preferably in amounts of 0.1% by weight to 5% by weight and particularly preferably in amounts of 0.5 to 2% by weight. The person skilled in the art is presented with absolutely no difficulties in selecting the amounts correspondingly depending on the intended action of the preparation.

In the preparations described which, in accordance with the invention, comprise at least one compound of the formula I, coloured pigments may furthermore also be present, where the layer structure of the pigments is not limited.

The coloured pigment should preferably be skin-coloured or brownish on use of 0.5 to 5% by weight. The choice of a corresponding pigment is familiar to the person skilled in the art.

Besides the compounds of the formula I and any other ingredients, preferred preparations comprise further organic UV filters, so-called hydrophilic or lipophilic sun-protection filters, which are effective in the UVA region and/or UVB region and/or IR and/or VIS region (absorbers). These substances can be selected, in particular, from cinnamic acid derivatives, salicylic acid derivatives, camphor derivatives, triazine derivatives, β,β-diphenylacrylate derivatives, p-aminobenzoic acid derivatives and polymeric filters and silicone filters, which are described in the application WO 93/04665. Further examples of organic filters are indicated in the patent application EP-A 0 487 404. The said UV filters are usually named below in accordance with INCI nomenclature.

Particularly suitable for a combination are:
para-aminobenzoic acid and derivatives thereof: PABA, Ethyl PABA, Ethyl dihydroxypropyl PABA, Ethylhexyl dimethyl PABA, for example marketed under the name "Escalol 507" by ISP, Glyceryl PABA, PEG-25 PABA, for example marketed under the name "Uvinul P25" by BASF.

Salicylates: Homosalate marketed by Merck under the name "Eusolex HMS"; Ethylhexyl salicylate, for example marketed by Haarmann and Reimer under the name "Neo Heliopan OS", Dipropylene glycol salicylate, for example marketed by Scher under the name "Dipsal", TEA salicylate, for example marketed by Haarmann and Reimer under the name "Neo Heliopan TS".

β,β-Diphenylacrylate derivatives: Octocrylene, for example marketed by Merck under the name "Eusolex OCR", "Uvinul N539" from BASF, etocrylene, for example marketed by BASF under the name "Uvinul N35".

Benzophenone derivatives: Benzophenone-1, for example marketed under the name "Uvinul 400"; Benzophenone-2, for example marketed under the name "Uvinul D50"; Benzophenone-3 or Oxybenzone, for example marketed under the name "Uvinul M40"; Benzophenone-4, for example marketed under the name "Uvinul MS40"; Benzophenone-9, for example marketed by BASF under the name "Uvinul DS-49", Benzophenone-5, Benzophenone-6, for example marketed by Norquay under the name "Helisorb 11", Benzophenone-8, for example marketed by American Cyanamid under the name "Spectra-Sorb UV-24", Benzophenone-12 n-hexyl Triazine derivatives: Ethylhexyltriazone, for example marketed by BASF under the name "Uvinul T150", Diethylhexylbutamidotriazone, for example marketed by Sigma 3V under the name "Uvasorb HEB", 2,4,6-tris(diisobutyl 4'-aminobenzalmalonate)-s-triazine or 2,4,6-tris(biphenyl)-1,3,5-triazine.

Anthraniline derivatives: Menthyl anthranilate, for example marketed by Haarmann and Reimer under the name "Neo Heliopan MA".

Imidazole derivatives: ethylhexyldimethoxybenzylidenedioxoimidazoline propionate.

Benzalmalonate derivatives: polyorganosiloxanes containing functional benzalmalonate groups, such as, for example, polysilicone-15, for example marketed by Hoffmann LaRoche under the name "Parsol SLX".

4,4-Diarylbutadiene derivatives: 1,1-Dicarboxy(2,2'-dimethylpropyl)-4,4-diphenylbutadiene.

Benzoxazole derivatives: 2,4-bis[5-(1-dimethylpropyl)benzoxazol-2-yl(4-phenyl)imino]-6-(2-ethylhexyl)imino-1,3,5-triazine, for example marketed by Sigma 3V under the name Uvasorb K2A, and mixtures comprising this.

Piperazine derivatives, such as, for example, the compound

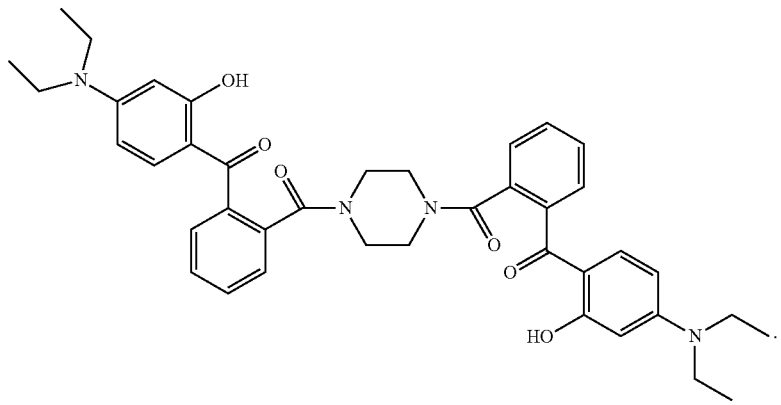 [SMILES: CCN(CC)c1ccc(C(=O)c2ccccc2C(=O)N2CCN(C(=O)c3ccccc3C(=O)c3ccc(N(CC)CC)cc3O)CC2)c(O)c1]

2-(4-diethyl-amino-2-hydroxybenzoyl)benzoate or 2-hydroxy-4-methoxybenzophenone, marketed by Merck, Darmstadt, under the name Eusolex® 4360.

Benzylidenecamphor derivatives: 3-Benzylidenecamphor, for example marketed under the name "Mexoryl SD" by Chimex, 4-Methylbenzylidene-camphor, for example marketed by Merck under the name "Eusolex 6300", benzylidenecamphorsulfonic acid, for example marketed by Chimex under the name "Mexoryl SL", Camphor benzalkonium methosulfate, for example marketed by Chimex under the name "Mexoryl SO", terephthalylidenedicamphorsulfonic acid, for example marketed by Chimex under the name "Mexoryl SX", Polyacrylamidomethylbenzylidenecamphor marketed by Chimex under the name "Mexoryl SW".

Phenylbenzimidazole derivatives: phenylbenzimidazolesulfonic acid, for example marketed by Merck under the name "Eusolex 232", disodium phenyl dibenzimidazole tetrasulfonate, for example marketed by Haarmann and Reimer under the name "Neo Heliopan AP".

Phenylbenzotriazole derivatives: Drometrizole trisiloxane, for example marketed by Rhodia Chimie under the name "Silatrizole", Methylenebis(benzotriazolyl)tetramethylbutylphenol in solid form, for example marketed by Fairmount Chemical under the name "MIXXIM BB/100", or in micronised form as an aqueous dispersion, for example marketed by Ciba Specialty Chemicals under the name "Tinosorb M".

The compounds listed should only be regarded as examples. It is of course also possible to use other UV filters.

Suitable organic UV-protecting substances can preferably be selected from the following list: Ethylhexyl salicylate, Phenylbenzimidazolesulfonic acid, Benzophenone-3, Benzophenone-4, Benzophenone-5, n-Hexyl 2-(4-diethylamino-2-hydroxybenzoyl)benzoate, 4-Methylbenzylidenecamphor, Terephthalylidenedicamphorsulfonic acid, Disodium phenyldibenzimidazoletetrasulfonate, Methylenebis(benzotriazolyl)tetramethylbutylphenol, Ethylhexyl Triazone, Diethylhexyl Butamido Triazone, Drometrizole trisiloxane, Polysilicone-15,1,1-Dicarboxy(2,2'-dimethylpropyl)-4,4-diphenylbutadiene, 2,4-Bis[5-(1-dimethylpropyl)benzoxazol-2-yl(4-phenyl)-imino]-6-(2-ethylhexyl) imino-1,3,5-triazine and mixtures thereof.

These organic UV filters are generally incorporated into formulations in an amount of 0.01 percent by weight to 20 percent by weight, preferably 1% by weight-10% by weight.

Besides the compounds of the formula I and any other organic UV filters, as described above, preferred preparations comprise further inorganic UV filters, so-called particulate UV filters.

These combinations with particulate UV filters are possible both as a powder and also as a dispersion or paste of the following types.

Preference is given here both to those from the group of the titanium dioxides, such as, for example, coated titanium dioxide (for example Eusolex®T-2000, Eusolex®T-AQUA, Eusolex®T-AVO, Eusolex®T-OLEO), zinc oxides (for example Sachtotec®), iron oxides or also cerium oxides and/or zirconium oxides.

Furthermore, combinations with pigmentary titanium dioxide or zinc oxide are also possible, where the particle size of these pigments is greater than or equal to 200 nm, for example Hombitec® COS.

It may furthermore be preferred for the preparations to comprise inorganic UV filters which have been aftertreated by conventional methods, as described, for example, in Cosmetics & Toiletries, February 1990, Vol. 105, pp. 53-64. One or more of the following aftertreatment components can be selected here: amino acids, beeswax, fatty acids, fatty acid alcohols, anionic surfactants, lecithin, phospholipids, sodium, potassium, zinc, iron or aluminium salts of fatty acids, polyethylenes, silicones, proteins (particularly collagen or elastin), alkanolamines, silicon dioxide, aluminium oxide, further metal oxides, phosphates, such as sodium hexametaphosphate, or glycerin.

Particulate UV filters which are preferably employed here are:
- untreated titanium dioxides, such as, for example, the products Microtitanium Dioxide MT 500 B from Tayca; titanium dioxide P25 from Degussa,
- aftertreated micronised titanium dioxides with aluminium oxide and silicon dioxide aftertreatment, such as, for example, the product "Microtitanium Dioxide MT 100 SA" from Tayca; or the product "Tioveil Fin" from Uniqema,
- aftertreated micronised titanium dioxides with aluminium oxide and/or aluminium stearate/laurate aftertreatment, such as, for example, Microtitanium Dioxide MT 100 T from Tayca, Eusolex T-2000 from Merck,
- aftertreated micronised titanium dioxides with iron oxide and/or iron stearate aftertreatment, such as, for example, the product "Microtitanium Dioxide MT 100 F" from Tayca,
- aftertreated micronised titanium dioxides with silicon dioxide, aluminium oxide and silicone aftertreatment, such as, for example, the product "Microtitanium Dioxide MT 100 SAS" from Tayca,
- aftertreated micronised titanium dioxides with sodium hexametaphosphates, such as, for example, the product "Microtitanium Dioxide MT 150 W" from Tayca.

The treated micronised titanium dioxides employed for the combination may also be aftertreated with:
- octyltrimethoxysilanes; such as, for example, the product Tego Sun T 805 from Degussa,
- silicon dioxide; such as, for example, the product Parsol T-X from DSM,
- aluminium oxide and stearic acid; such as, for example, the product UV-Titan M160 from Kemira,
- aluminium and glycerin; such as, for example, the product UV-Titan from Kemira,
- aluminium and silicone oils, such as, for example, the product UV-Titan M262 from Kemira,
- sodium hexametaphosphate and polyvinylpyrrolidone,
- polydimethylsiloxanes, such as, for example, the product 70250 Cardre UF TiO2S13 from Cardre,
- polydimethylhydrogenosiloxanes, such as, for example, the product Microtitanium Dioxide USP Grade Hydrophobic from Color Techniques.

The combination with the following products may furthermore also be advantageous:
- untreated zinc oxides, such as, for example, the product Z-Cote from BASF (Sunsmart), Nanox from Elementis
- aftertreated zinc oxides, such as, for example, the following products:
    "Zinc Oxide CS-5" from Toshibi (ZnO aftertreated with polymethylhydrogenosiloxanes)
    Nanogard Zinc Oxide FN from Nanophase Technologies
    "SPD-Z1" from Shin-Etsu (ZnO aftertreated with a silicone-grafted acrylic polymer, dispersed in cyclodimethylsiloxanes)
    "Escalol Z100" from ISP (aluminium oxide-aftertreated ZnO dispersed in an ethylhexyl methoxycinnamate/PVP-hexadecene/methicone copolymer mixture)
    "Fuji ZNO-SMS-10" from Fuji Pigment (ZnO aftertreated with silicon dioxide and polymethylsilsesquioxane)
- untreated cerium oxide micropigment, for example with the name "Colloidal Cerium Oxide" from Rhone Poulenc
- untreated and/or aftertreated iron oxides with the name Nanogar from Arnaud.

For example, it is also possible to employ mixtures of various metal oxides, such as, for example, titanium dioxide and cerium oxide, with and without aftertreatment, such as, for example, the product Sunveil A from Ikeda. In addition, it is also possible to use mixtures of aluminium oxide, silicon dioxide and silicone-aftertreated titanium dioxide, zinc oxide mixtures, such as, for example, the product UV-Titan M261 from Kemira, in combination with the UV protection agent according to the invention.

These inorganic UV filters are generally incorporated into the preparations in an amount of 0.1 percent by weight to 25 percent by weight, preferably 2% by weight-10% by weight.

By combination of one or more of the said compounds having a UV filter action, the protective action against harmful effects of the UV radiation can be optimised.

All the said UV filters can also be employed in encapsulated form. In particular, it is advantageous to employ organic UV filters in encapsulated form. In detail, the following advantages arise:

The hydrophilicity of the capsule wall can be set independently of the solubility of the UV filter. Thus, for example, it is also possible to incorporate hydrophobic UV filters into purely aqueous preparations. In addition, the oily impression on application of the preparation comprising hydrophobic UV filters, which is frequently regarded as unpleasant, is suppressed.

Certain UV filters, in particular dibenzoylmethane derivatives, exhibit only reduced photostability in cosmetic preparations. Encapsulation of these filters or compounds which impair the photostability of these filters, such as, for example, cinnamic acid derivatives, enables the photostability of the entire preparation to be increased.

Skin penetration by organic UV filters and the associated potential for irritation on direct application to the human skin is repeatedly being discussed in the literature. The encapsulation of the corresponding substances which is proposed here suppresses this effect.

In general, encapsulation of individual UV filters or other ingredients enables preparation problems caused by the interaction of individual preparation constituents with one another, such as crystallisation processes, precipitation and agglomeration, to be avoided since the interaction is suppressed.

It is therefore preferred for one or more of the above-mentioned UV filters to be in encapsulated form. It is advantageous here for the capsules to be so small that they cannot be observed with the naked eye. In order to achieve the above-mentioned effects, it is furthermore necessary for the capsules to be sufficiently stable and the encapsulated active compound (UV filter) only to be released to the environment to a small extent, or not at all.

Suitable capsules can have walls of inorganic or organic polymers. For example, U.S. Pat. No. 6,242,099 B1 describes the production of suitable capsules with walls of chitin, chitin derivatives or polyhydroxylated polyamines. Capsule walls may also consist of PMMA. Capsules particularly preferably to be employed have walls which can be obtained by a sol-gel process, as described in the applications WO 00/09652, WO 00/72806 and WO 00/71084. Preference is in turn given here to capsules whose walls are built up from silica gel (silica; undefined silicon oxide hydroxide). The production of corresponding capsules is known to the person skilled in the art, for example from the cited patent applications, whose contents expressly also belong to the subject-matter of the present application.

The capsules are preferably present in preparations to be employed in accordance with the invention in amounts which ensure that the encapsulated UV filters are present in the preparation in the above-indicated percent by weight ratios.

Preferred preparations may likewise comprise at least one further ascorbic acid derivative, preferably from the group ascorbic acid, magnesium ascorbyl phosphate or ascorbyl palmitate.

Preferred preparations may also comprise at least one further cosmetic active compound, for example selected from antioxidants, anti-ageing active compounds, anti-cellulite active compounds, self-tanning substances, skin-lightening active compounds or vitamins.

The protective action of preparations against oxidative stress or against the effect of free radicals can be improved if the preparations comprise one or more antioxidants, the person skilled in the art being presented with absolutely no difficulties in selecting antioxidants which act suitably quickly or with a time delay.

There are many proven substances known from the specialist literature which can be used as antioxidants, for example amino acids (for example glycine, histidine, tyrosine, tryptophan) and derivatives thereof, imidazoles (for example urocanic acid) and derivatives thereof, peptides, such as D,L-carnosine, D-carnosine, L-carnosine and derivatives thereof (for example anserine, carotinoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homocysteine sulfoximine, buthionine sulfones, penta-, hexa- and heptathionine sulfoximine) in very low tolerated doses (for example pmol to µmmol/kg), and also (metal) chelating agents (for example α-hydroxyfatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), vitamin A and derivatives (for example vitamin A palmitate), and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiaretic acid, trihydroxybutyrophenone, quercetin, uric acid and derivatives thereof, mannose and derivatives thereof, zinc and derivatives thereof (for example ZnO, ZnSO$_4$), selenium and derivatives thereof (for example selenomethionine), stilbenes and derivatives thereof (for example stilbene oxide, trans-stilbene oxide).

EDTA, in particular disodium EDTA, is also a chelating agent and preferably, in combination with the compounds of the formula I according to the invention or also with 4-methoxycinnamoyl 6O-ascorbate, has the property of stabilising the compounds of the formula I or 4-methoxycinnamoyl 6O-ascorbate in the preparation and/or reducing or preventing discoloration of the cosmetic formulation. EDTA denotes ethylenediamine tetraacetate.

Other suitable chelating agents having this property are pentasodium ethylenediaminetetramethylenephosphonate. However, chelating agents which belong to the group of the polyamines or alpha-hydroxyfatty acids are also suitable.

Suitable antioxidants are also compounds of the formula A or B

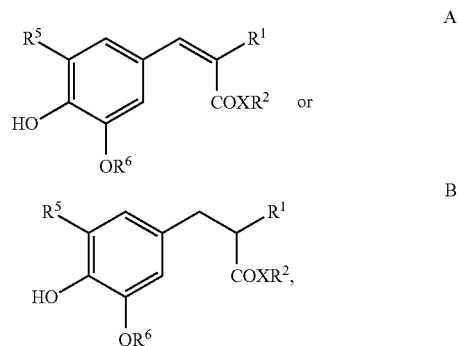

in which
$R^1$ can be selected from the group —C(O)CH$_3$, —CO$_2$R$^3$, —C(O)NH$_2$ and —C(O)N(R$^4$)$_2$,
X denotes O or NH,
$R^2$ denotes linear or branched alkyl having 1 to 30 C atoms,
$R^3$ denotes linear or branched alkyl having 1 to 20 C atoms,
$R^4$ in each case, independently of one another, denotes H or linear or branched alkyl having 1 to 8 C atoms,
$R^5$ denotes H, linear or branched alkyl having 1 to 8 C atoms or linear or branched alkoxy having 1 to 8 C atoms, and
$R^6$ denotes linear or branched alkyl having 1 to 8 C atoms, preferably derivatives of 2-(4-hydroxy-3,5-dimethoxybenzylidene)malonic acid and/or 2-(4-hydroxy-3,5-dimethoxybenzyl)malonic acid, particularly preferably bis (2-ethylhexyl) 2-(4-hydroxy-3,5-dimethoxybenzylidene) malonate (for example Oxynex® ST Liquid) and/or bis(2-ethylhexyl) 2-(4-hydroxy-3,5-dimethoxybenzyl)malonate (for example RonaCare® AP).

Mixtures of antioxidants are likewise suitable for use in the cosmetic preparations according to the invention. Known and commercial mixtures are, for example, mixtures comprising, as active compounds, lecithin, L-(+)-ascorbyl palmitate and citric acid, natural tocopherols, L-(+)-ascorbyl palmitate, L-(+)-ascorbic acid and citric acid (for example Oxynex® K LIQUID), tocopherol extracts from natural sources, L-(+)-ascorbyl palmitate, L-(+)-ascorbic acid and citric acid (for example Oxynex® L LIQUID), DL-α-tocopherol, L-(+)-ascorbyl palmitate, citric acid and lecithin (for example Oxynex® LM) or butylhydroxytoluene (BHT), L-(+)-ascorbyl palmitate and citric acid (for example Oxynex® 2004). Antioxidants of this type are usually employed in such compositions with the compounds according to the invention in percent by weight ratios in the range from 1000:1 to 1:1000, preferably in percent by weight ratios from 100:1 to 1:100.

Of the phenols which can be used in accordance with the invention, the polyphenols, some of which are naturally occurring, are of particular interest for applications in the pharmaceutical, cosmetic or nutrition sector. For example, the flavonoids or bioflavonoids, which are principally known as plant dyes, frequently have an antioxidant potential. K. Lemanska, H. Szymusiak, B. Tyrakowska, R. Zielinski, I. M. C. M. Rietjens; Current Topics in Biophysics 2000, 24(2), 101-108, are concerned with effects of the substitution pattern of mono- and dihydroxyflavones. It is observed therein that dihydroxyflavones containing an OH group adjacent to the keto function or OH groups in the 3',4'- or 6,7- or 7,8-position have antioxidative properties, while other mono- and dihydroxyflavones in some cases do not have antioxidative properties.

Quercetin (cyanidanol, cyanidenolon 1522, meletin, sophoretin, ericin, 3,3',4',5,7-pentahydroxyflavone) is frequently mentioned as a particularly effective antioxidant (for example C. A. Rice-Evans, N. J. Miller, G. Paganga, Trends in Plant Science 1997, 2(4), 152-159). K. Lemanska, H. Szymusiak, B. Tyrakowska, R. Zielinski, A. E. M. F. Soffers and I. M. C. M. Rietjens, Free Radical Biology & Medicine 2001, 31(7), 869-881, have investigated the pH dependence of the antioxidant action of hydroxyflavones. Quercetin exhibits the highest activity amongst the structures investigated over the entire pH range.

Suitable anti-ageing active compounds, in particular for skin-care preparations, are preferably so-called compatible solutes. These are substances which are involved in the osmoregulation of plants or microorganisms and can be isolated from these organisms. The generic term compatible solutes here also encompasses the osmolytes described in German patent application DE-A-10133202. Suitable osmolytes are, for example, the polyols, methylamine compounds and amino acids and respective precursors thereof. Osmolytes in the sense of German patent application DE-A-10133202 are taken to mean, in particular, substances from the group of the polyols, such as, for example, myo-inositol, mannitol or sorbitol, and/or one or more of the osmolytically active substances mentioned below: taurine, choline, betaine, phosphorylcholine, glycerophosphorylcholines, glutamine, glycine, α-alanine, glutamate, aspartate and proline. Precursors of these substances are, for example, glucose, glucose polymers, phosphatidylcholine, phosphatidylinositol, inorganic phosphates, proteins, peptides and polyamino acids. Precursors are, for example, compounds which are converted into osmolytes by metabolic steps.

Compatible solutes which are preferably employed in accordance with the invention are substances selected from the group consisting of pyrimidine-carboxylic acids (such as ectoin and hydroxyectoin), proline, betaine, glutamine, cyclic diphosphoglycerate, N-acetylornithine, trimethylamine N-oxide, di-myo-inositol phosphate (DIP), cyclic 2,3-diphosphoglycerate (cDPG), 1,1-diglycerol phosphate (DGP), β-mannosyl glycerate (firoin), β-mannosyl glyceramide (firoin-A) and/or dimannosyl diinositol phosphate (DMIP) or an optical isomer, derivative, for example an acid, a salt or ester, of these compounds, or combinations thereof.

Of the pyrimidinecarboxylic acids, particular mention should be made here of ectoin ((S)-1,4,5,6-tetrahydro-2-methyl-4-pyrimidinecarboxylic acid) and hydroxyectoin ((S,S)-1,4,5,6-tetrahydro-5-hydroxy-2-methyl-4-pyrimidine-carboxylic acid) and derivatives thereof.

Furthermore, the preparations according to the invention may comprise at least one self-tanning agent as further ingredient.

Advantageous self-tanning agents which can be employed are, inter alia: 1,3-dihydroxyacetone, glycerolaldehyde, hydroxymethylglyoxal, γ-dialdehyde, erythrulose, 6-aldo-D-fructose, ninhydrin, 5-hydroxy-1,4-naphthoquinone (juglone) or 2-hydroxy-1,4-naphthoquinone (lawsone). Very particular preference is given to 1,3-dihydroxyacetone, erythrulose or a combination thereof.

The preparations may also comprise one or more further skin-lightening active compounds or synonymously depigmentation active compounds. Skin-lightening active compounds can in principle be all active compounds known to the person skilled in the art. Examples of compounds having skin-lightening activity are hydroquinone, kojic acid, arbutin, aloesin or rucinol.

The preparations to be employed may comprise vitamins as further ingredients. Preference is given to vitamins and vitamin derivatives selected from vitamin A, vitamin A propionate, vitamin A palmitate, vitamin A acetate, retinol, vitamin B, thiamine chloride hydrochloride (vitamin $B_1$), riboflavin (vitamin $B_2$), nicotinamide, vitamin C (ascorbic acid), vitamin D, ergocalciferol (vitamin $D_2$), vitamin E, DL-α-tocopherol, tocopherol E acetate, tocopherol hydrogensuccinate, vitamin $K_1$, esculin (vitamin P active compound), thiamine (vitamin $B_1$), nicotinic acid (niacin), pyridoxine, pyridoxal, pyridoxamine (vitamin $B_6$), pantothenic acid, biotin, folic acid and cobalamine (vitamin $B_{12}$, particularly preferably vitamin A palmitate, vitamin C and derivatives thereof, DL-α-tocopherol, tocopherol E acetate, nicotinic acid, pantothenic acid and biotin. In cosmetic applications, vitamins are usually added with the flavonoid-containing premixes or preparations in ranges from 0.01 to 5.0% by weight, based on the total weight. Nutrition-physiological applications are oriented towards the respective recommended vitamin demand.

The retinoids described are at the same time also effective anti-cellulite active compounds. A likewise known anti-cellulite active compound is caffeine.

The said constituents of the preparation can be incorporated in the usual manner, with the aid of techniques which are well known to the person skilled in the art.

Suitable preparations are those for external application, for example can be sprayed onto the skin as cream or milk (O/W, W/O, O/W/O, W/O/W), as lotion or emulsion, in the form of oily-alcoholic, oily-aqueous or aqueous-alcoholic gels or solutions. They can be in the form of solid sticks or formulated as an aerosol. Administration forms such as capsules, dragees, powders, tablet solutions or solutions are suitable for internal use.

Examples which may be mentioned of application forms of the preparations to be employed are: solutions, suspensions, emulsions, PIT emulsions, pastes, ointments, gels, creams, lotions, powders, soaps, surfactant-containing cleansing preparations, oils, aerosols and sprays.

Preferred assistants originate from the group of preservatives, stabilisers, solubilisers, colorants, odour improvers.

Ointments, pastes, creams and gels may comprise the customary vehicles which are suitable for topical application, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary vehicles, for example lactose, talc, silica, aluminium hydroxide, calcium silicate and polyamide powder, or mixtures of these substances. Sprays may additionally comprise the customary readily volatile, liquefied propellants, for example chlorofluorocarbons, propane/butane or dimethyl ether. Compressed air can also advantageously be used.

Solutions and emulsions may comprise the customary vehicles, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, peanut oil, wheatgerm oil, olive oil, castor oil and sesame oil, glycerol fatty acid esters, polyethylene glycols and fatty acid esters of sorbitan, or mixtures of these substances.

A preferred solubiliser in general is 2-isopropyl-5-methyl-cyclohexane-carbonyl-D-alanine methyl ester.

Suspensions may comprise the customary vehicles, such as liquid diluents, for example water, ethanol or propylene glycol, suspension media, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Soaps may comprise the customary vehicles, such as alkali metal salts of fatty acids, salts of fatty acid monoesters, fatty acid protein hydrolysates, isothionates, lanolin, fatty alcohol, vegetable oils, plant extracts, glycerol, sugars, or mixtures of these substances.

Surfactant-containing cleansing products may comprise the customary vehicles, such as salts of fatty alcohol sulfates, fatty alcohol ether sulfates, sulfosuccinic acid monoesters, fatty acid protein hydrolysates, isothionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters, or mixtures of these substances.

Face and body oils may comprise the customary vehicles, such as synthetic oils, such as fatty acid esters, fatty alcohols, silicone oils, natural oils, such as vegetable oils and oily plant extracts, paraffin oils, lanolin oils, or mixtures of these substances.

Further typical cosmetic application forms are also lipsticks, lip-care sticks, powder make-up, emulsion make-up and wax make-up, and sunscreen, pre-sun and after-sun preparations.

The preferred preparation forms also include, in particular, emulsions.

Emulsions are advantageous and comprise, for example, the said fats, oils, waxes and other fatty substances, as well as water and an emulsifier, as usually used for a preparation of this type.

It has been found that the compounds of the formula I according to the invention, but also 4-methoxycinnamoyl 6O-ascorbate, can particularly preferably be incorporated into preparations with polar oil components.

Particularly preferred polar oil components are, for example, arylalkyl benzoates, dimethylisosorbide, phthalimides, fatty acid esters, alkyl benzoates, triglycerides or N,N-disubstituted amides.

A particularly preferred arylalkyl benzoate is 2-phenylethyl benzoate, which is commercially available under the name X-Tend™ 226 from ISP.

Particularly preferred phthalimides are, for example, n-butylphthalimide, isopropylphthalimide or mixtures of butylphthalimide and isopropylphthalimide. A specific mixture is available, for example, under the commercial product Pelemol® BIP from Phoenix Chemicals.

Preferred fatty acid esters are, for example, dimyristyl tartrate, available as COSMACOL® ETLP from Sasol, citric acid esters containing alkyl groups having 14 or 15 C atoms each, available as COSMACOL® ECL from Sasol, citric acid esters containing alkyl groups having 12 or 13 C atoms each, available as COSMACOL® ECI from Sasol, lactic acid esters containing alkyl groups having 12 to 13 C atoms each, available as COSMACOL® ELI, tridecyl salicylate, available as COSMACOL® ESI, esters of ethylhexanoic acid containing alkyl groups having 12 to 13 C atoms each, available as COSMACOL® EOI from Sasol, maleic acid esters containing alkyl groups having 12 to 13 C atoms each, available as COSMACOL® EMI, tartaric acid esters containing alkyl groups having 12 to 13 C atoms each, available as COSMACOL® ETI from Sasol.

Preferred alkyl benzoates are benzoic acid esters containing alkyl groups having 12 to 15 C atoms each. Commercial products are available as COSMACOL® EBI from Sasol or as Fins® Iv® TN from Finetex.

Preferred triglycerides are triglycerides with fatty acids having 8 to 12 C atoms each, for example available as Miglyol® 812 from Evonik.

N,N-disubstituted amides are described, for example, in EP 1044676 or EP 0928608. Preferred N,N-disubstituted amides are N-acetyl-N-butylamino-propionate, for example available as IR3535 from Merck, isopropyl N-lauroylsarcosinate, available as Eldew® SL-205 from Ajimoto, or N,N-diethyltoluamide, available as Deet® from Showa Denko.

The lipid phase may advantageously be selected from the following group of substances:
mineral oils, mineral waxes;
oils, such as triglycerides of capric or caprylic acid, furthermore natural oils, such as, for example, castor oil;
fats, waxes and other natural and synthetic fatty substances, preferably esters of fatty acids with alcohols having a low carbon number, for example with isopropanol, propylene glycol or glycerol, or esters of fatty alcohols with alkanoic acids having a low carbon number or with fatty acids;
silicone oils, such as dimethylpolysiloxanes, diethylpolysiloxanes, diphenylpolysiloxanes and mixed forms thereof.

For the purposes of the present invention, the oil phase of the emulsions, oleogels or hydrodispersions or lipodispersions is advantageously selected from the group of esters of saturated and/or unsaturated, branched and/or unbranched alkanecarboxylic acids having a chain length of 3 to 30 C atoms and saturated and/or unsaturated, branched and/or unbranched alcohols having a chain length of 3 to 30 C atoms, or from the group of esters of aromatic carboxylic acids and saturated and/or unsaturated, branched and/or unbranched alcohols having a chain length of 3 to 30 C atoms. Ester oils of this type can then advantageously be selected from the group of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of esters of this type, for example jojoba oil.

The oil phase may furthermore advantageously be selected from the group of branched and unbranched hydrocarbons and hydrocarbon waxes, silicone oils, dialkyl ethers, or the group of saturated or unsaturated, branched or unbranched alcohols, and fatty acid triglycerides, specifically the triglycerol esters of saturated and/or unsaturated, branched and/or unbranched alkanecarboxylic acids having a chain length of 8 to 24, in particular 12-18 C atoms. The fatty acid triglycerides may advantageously be selected, for example, from the group of synthetic, semi-synthetic and natural oils, for example olive oil, sunflower oil, soya oil, peanut oil, rapeseed oil, almond oil, palm oil, coconut oil, palm kernel oil and the like.

Any desired mixtures of oil and wax components of this type may also advantageously be employed for the purposes of the present invention. It may also be advantageous to employ waxes, for example cetyl palmitate, as the only lipid component of the oil phase.

The aqueous phase of the preparations to be employed optionally advantageously comprises alcohols, diols or polyols having a low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols having a low carbon number, for example ethanol, isopropanol, 1,2-propanediol, glycerol, and, in particular, one or more thickeners, which may advantageously be selected from the group of silicon dioxide, aluminium silicates, polysaccharides and derivatives thereof, for example hyaluronic acid, xanthan gum, hydroxypropylmethylcellulose, particularly advantageously from the group of the polyacrylates, preferably a polyacrylate from the group of the so-called Carbopols, for example Carbopol grades 980, 981, 1382, 2984, 5984, in each case individually or in combination.

In particular, mixtures of the above-mentioned solvents are used. In the case of alcoholic solvents, water may be a further constituent.

Emulsions are advantageous and comprise, for example, the said fats, oils, waxes and other fatty substances, as well as water and an emulsifier, as usually used for a formulation of this type.

In a preferred embodiment, the preparations to be employed comprise hydrophilic surfactants. The hydrophilic surfactants are preferably selected from the group of the alkylglucosides, acyl lactylates, betaines and coconut amphoacetates.

It is likewise advantageous to employ natural or synthetic raw materials and assistants or mixtures which are distinguished by an effective content of the active compounds used in accordance with the invention, for example Plantaren® 1200 (Henkel KGaA), Oramix® NS 10 (Seppic).

The cosmetic and dermatological preparations may exist in various forms. Thus, they may be, for example, a solution, a water-free preparation, an emulsion or microemulsion of the water-in-oil (W/O) type or of the oil-in-water (O/W) type, a multiple emulsion, for example of the water-in-oil-in-water (W/O/W) type, a gel, a solid stick, an ointment or an aerosol. It is also advantageous to administer ectoins in encapsulated form, for example in collagen matrices and other conventional encapsulation materials, for example as cellulose encapsulations, in gelatine, wax matrices or liposomally encapsulated. In particular, wax matrices, as described in DE-A-43 08 282, have proven favourable. Preference is given to emulsions. O/W emulsions are particularly preferred. Emulsions, W/O emulsions and O/W emulsions are obtainable in a conventional manner.

Emulsifiers that can be used are, for example, the known W/O and O/W emulsifiers. It is advantageous to use further conventional co-emulsifiers in the preferred O/W emulsions.

The co-emulsifiers selected are advantageously, for example, O/W emulsifiers, principally from the group of substances having HLB values of 11-16, very particularly advantageously having HLB values of 14.5-15.5, so long as the O/W emulsifiers have saturated radicals R and R'. If the O/W emulsifiers have unsaturated radicals R and/or R' or if isoalkyl derivatives are present, the preferred HLB value of such emulsifiers may also be lower or higher.

It is advantageous to select the fatty alcohol ethoxylates from the group of ethoxylated stearyl alcohols, cetyl alcohols, cetylstearyl alcohols (cetearyl alcohols).

It is furthermore advantageous to select the fatty acid ethoxylates from the following group:
polyethylene glycol (20) stearate, polyethylene glycol (21) stearate, polyethylene glycol (22) stearate, polyethylene glycol (23) stearate, polyethylene glycol (24) stearate, polyethylene glycol (25) stearate, polyethylene glycol (12) isostearate, polyethylene glycol (13) isostearate, polyethylene glycol (14) isostearate, polyethylene glycol (15) isostearate, polyethylene glycol (16) isostearate, polyethylene glycol (17) isostearate, polyethylene glycol (18) isostearate, polyethylene glycol (19) isostearate, polyethylene glycol (20) isostearate, polyethylene glycol (21) isostearate, polyethylene glycol (22) isostearate, polyethylene glycol (23) isostearate, polyethylene glycol (24) isostearate, polyethylene glycol (25) isostearate, polyethylene glycol (12) oleate, polyethylene glycol (13) oleate, polyethylene glycol (14) oleate, polyethylene glycol (15) oleate, polyethylene glycol (16) oleate, polyethylene glycol (17) oleate, polyethylene glycol (18) oleate, polyethylene glycol (19) oleate, polyethylene glycol (20) oleate.

An ethoxylated alkyl ether carboxylic acid or salt thereof which can advantageously be used is sodium laureth-11 carboxylate. An alkyl ether sulfate which can advantageously be used is sodium laureth-14 sulfate. An ethoxylated cholesterol derivative which can advantageously be used is polyethylene glycol (30) cholesteryl ether. Polyethylene glycol (25) soyasterol has also proven successful. Ethoxylated triglycerides which can advantageously be used are the polyethylene glycol (60) evening primrose glycerides.

It is furthermore advantageous to select the polyethylene glycol glycerol fatty acid esters from the group of polyethylene glycol (20) glyceryl laurate, polyethylene glycol (21) glyceryl laurate, polyethylene glycol (22) glyceryl laurate, polyethylene glycol (23) glyceryl laurate, polyethylene glycol (6) glyceryl caprate/caprinate, polyethylene glycol (20) glyceryl oleate, polyethylene glycol (20) glyceryl isostearate, polyethylene glycol (18) glyceryl oleate/cocoate.

It is likewise favourable to select the sorbitan esters from the group of polyethylene glycol (20) sorbitan monolaurate, polyethylene glycol (20) sorbitan monostearate, polyethylene glycol (20) sorbitan monoisostearate, polyethylene glycol (20) sorbitan monopalmitate, polyethylene glycol (20) sorbitan monooleate.

The following can be employed as optional W/O emulsifiers, but ones which may nevertheless be advantageous in accordance with the invention: fatty alcohols having 8 to 30 carbon atoms, monoglycerol esters of saturated and/or unsaturated, branched and/or unbranched alkanecarboxylic acids having a chain length of 8 to 24, in particular 12-18 C atoms, diglycerol esters of saturated and/or unsaturated, branched and/or unbranched alkanecarboxylic acids having a chain length of 8 to 24, in particular 12-18 C atoms, monoglycerol ethers of saturated and/or unsaturated, branched and/or unbranched alcohols having a chain length of 8 to 24, in particular 12-18 C atoms, diglycerol ethers of saturated and/or unsaturated, branched and/or unbranched alcohols having a chain length of 8 to 24, in particular 12-18 C atoms, propylene glycol esters of saturated and/or unsaturated, branched and/or unbranched alkanecarboxylic acids having a chain length of 8 to 24, in particular 12-18 C atoms, and sorbitan esters of saturated and/or unsaturated, branched and/or unbranched alkanecarboxylic acids having a chain length of 8 to 24, in particular 12-18 C atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprinate, glyceryl monocaprylate or PEG 30 dipolyhydroxystearate.

The preparation may comprise cosmetic adjuvants that are usually used in this type of preparation, such as, for example, thickeners, softeners, moisturisers, surface-active agents, emulsifiers, preservatives, antifoams, perfumes, waxes, lanolin, propellants, dyes and/or pigments, and other ingredients usually used in cosmetics.

The dispersant or solubiliser used can be an oil, wax or other fatty substance, a lower monoalcohol or a lower polyol or mixtures thereof. Particularly preferred monoalcohols or polyols include ethanol, i-propanol, propylene glycol, glycerol and sorbitol.

A preferred embodiment of the invention is an emulsion in the form of a protective cream or milk which comprises, for example, fatty alcohols, fatty acids, fatty acid esters, in particular triglycerides of fatty acids, lanolin, natural and synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycol, such as propylene glycol, and/or a polyol, such as glycerol, and oils, waxes and fatty acid esters, such as triglycerides of fatty acids.

The preparation may also be in the form of an alcoholic gel which comprises one or more lower alcohols or polyols, such as ethanol, propylene glycol or glycerol, and a thickener, such as siliceous earth. The oily-alcoholic gels also comprise natural or synthetic oil or wax.

The solid sticks consist of natural or synthetic waxes and oils, fatty alcohols, fatty acids, fatty acid esters, lanolin and other fatty substances.

If a preparation is formulated as an aerosol, use is generally made of the customary propellants, such as alkanes, fluoroalkanes and chlorofluoroalkanes, preferably alkanes.

Preferred preparations have a pH in the range from 3.5 to 7, particularly preferably in the range from 4.5 to 6.5. It has proven advantageous for the water phase employed for the formulation to be in buffered form. The use of a citrate buffer (citric acid/sodium citrate) is particularly preferred.

Even without further comments, it is assumed that a person skilled in the art will be able to utilise the above description in the broadest scope. The preferred embodiments and examples should therefore merely be regarded as descriptive disclosure which is absolutely not limiting in any way. The complete disclosure content of all applications and publications mentioned above and below is incorporated into this application by way of reference. The percent by weight ratios of the individual ingredients in the preparations of the examples expressly belong to the disclosure content of the description and can therefore be utilised as features.

The examples of the subject-matter according to the invention indicated below merely serve for explanation and do not narrow the present invention in any way. In addition, the invention described can be carried out through-out the range claimed. All compounds or components which can be used in the preparations are either known and commercially available or can be synthesised by known methods. In general, the INCI names of the raw materials used are indicated (the INCI names are by definition given in English).

SYNTHESIS EXAMPLES

Example 1

(S)-2-((R)-3,4-Dihydroxy-5-oxo-2,5-dihydrofuran-2-yl)-2-hydroxyethyl 3-(2,4-dimethoxyphenyl)acrylate by enzymatic esterification 2,4-dimethoxycinnamoyl 6-O-ascorbate

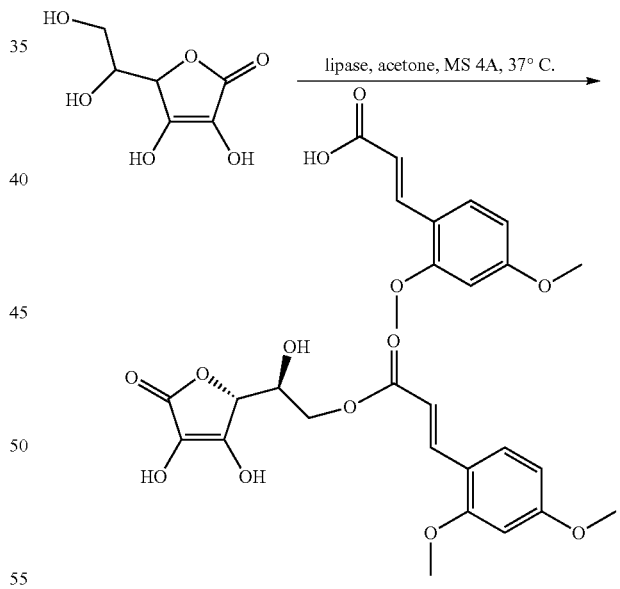

10 g of L-ascorbic acid (56.8 mmol; 1 eq.) in 190 ml of acetone are initially introduced with 10 g of molecular sieve 4 Å, and 100 mg of lipase (e.g. *Rhizomucor miehei*, recombinant from *Aspergillus oryzae* or *Candida cylindracea*) and then 29.6 g of 3-(2,4-dimethoxyphenyl)acrylic acid (141.9 mmol, 2.5 eq.) are added. After a reaction time of 18 hours at 37° C., the molecular sieve is filtered off, the mixture is cooled to room temperature, and the product is precipitated by slow addition of 100 ml of water. Drying at 60° C. in vacuo gives the product as a white solid.

Example 2

Synthesis of (R)-2-((R)-3,4-dihydroxy-5-oxo-2,5-dihydrofuran-2-yl)-2-hydroxyethyl (E)-3-(2,4,6-trimethoxyphenyl)acrylate 2,4,6-trimethoxycinnamoyl 6-O-ascorbate

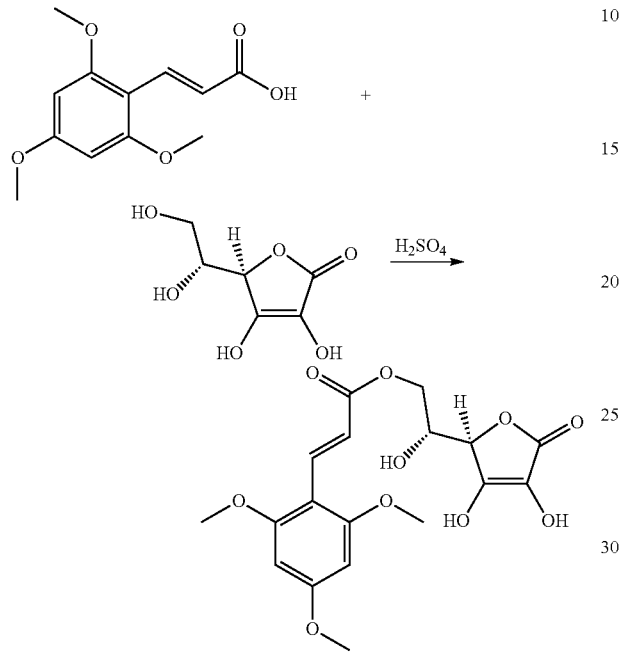

265 ml of conc. sulfuric acid are initially introduced into an argon-flushed three-necked flask and cooled to 0° C. 133.1 g (0.756 mol, 3 eq.) of ascorbic acid and subsequently 60 g of (E)-3-(2,4,6-trimethoxyphenyl)acrylic acid (0.252 mol, 1 eq.) are added in portions. 73.7 ml of oleum (sulfuric acid comprising 65% of $SO_3$) are then added dropwise. After a reaction time of 4 hours at 40° C., the reaction solution is poured onto 1000 g of ice, saturated with sodium chloride and extracted with methyl ethyl ketone. The combined org. phases are extracted with sat. NaCl solution, dried over sodium sulfate, and the solvent is removed in vacuo. Crystallisation from ethyl acetate gives the product as a pale-yellow solid.

$^1$H-NMR data of 2,4,6-TMCA [(E)-3-(2,4,6-trimethoxyphenyl)acrylic acid (R)-2-((R)-3,4-dihydroxy-5-oxo-2,5-dihydrofuran-2-yl)-2-hydroxyethyl ester]

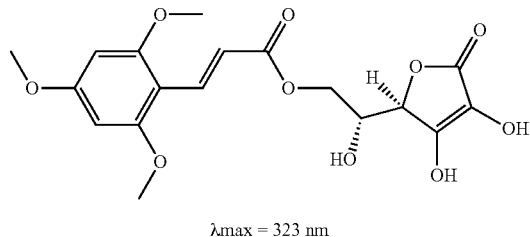 [SMILES: COc1cc(OC)c(/C=C/C(=O)OC[C@@H](O)[C@H]2OC(=O)C(O)=C2O)c(OC)c1]

λmax = 323 nm $^1$H-NMR (500 MHz, DMSO) δ 3.83 (s, $OCH_3$), 3.86 (s, 2×$OCH_3$), 4.03 (t, CH, J=1.6 Hz), 4.16 (m, $CH_2$), 4.72 (d, CH, J=1.3 Hz), 5.34 (br, OH), 6.28 (s, 2×CH), 6.65 (d, CH), 7.96 (d, CH), 8.39 (br, OH), 11.09 (br, OH).

Example 3

Synthesis of (R)-2-((R)-3,4-dihydroxy-5-oxo-2,5-dihydrofuran-2-yl)-2-hydroxyethyl (E)-3-(2,3,4-trimethoxyphenyl)acrylate 2,3,4-trimethoxycinnamoyl 6-O-ascorbate

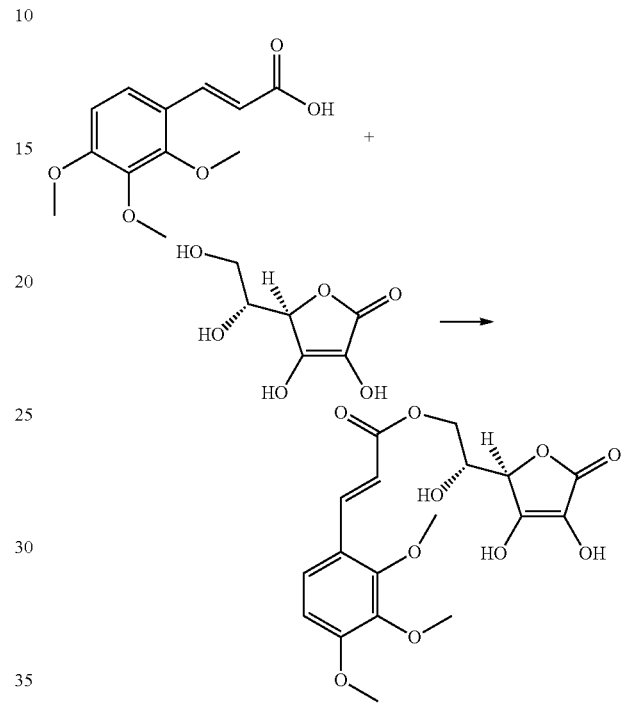

25 g of (E)-3-(2,3,4-trimethoxyphenyl)acrylic acid (105 mmol; 1 eq.) are dissolved in 100 ml of NMP at 25° C., 9.1 ml of thionyl chloride (126 mmol, 1.2 eq.) are added at 0° C., and the mixture is stirred for 2 hours. 55.4 g of ascorbic acid (315 mmol; 3 eq.) are subsequently added at 25-28° C., and the mixture is stirred for a further 60 min. Water and chloroform are subsequently added, the mixture is extracted and dried, and the solvent is removed in vacuo. The residue is recrystallised from toluene, giving the product as a pale-beige solid.

Example 4

Synthesis of (R)-2-((R)-3,4-dihydroxy-5-oxo-2,5-dihydrofuran-2-yl)-2-hydroxyethyl (E)-3-(2,4,5-trimethoxyphenyl)acrylate 2,4,5-trimethoxycinnamoyl 6-O-ascorbate

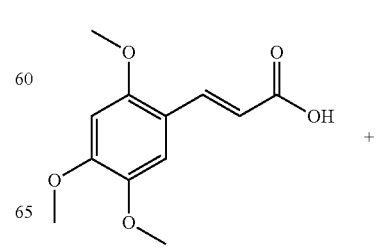

-continued

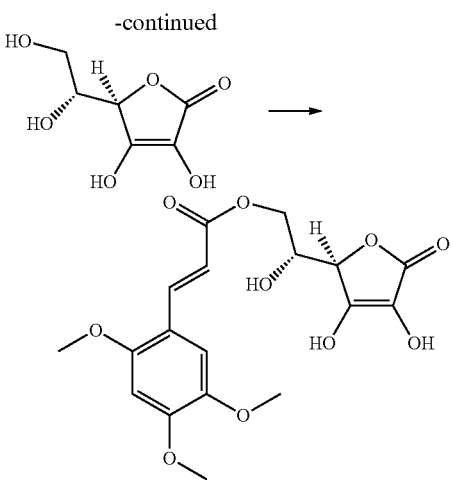

20 g of (E)-3-(2,4,5-trimethoxyphenyl)acrylic acid (84 mmol; 1 eq.) are dissolved in 100 ml of dimethylformamide in an argon-flushed three-necked flask, and 11.1 g of diisopropylcarbodiimide (88.1 mmol, 1.05 eq.) are added. After 30 min, ascorbic acid (22.2 g, 126 mmol; 1.5 eq.) dissolved in 45 ml of dimethylformamide is added dropwise. After 30 min at 0° C., the mixture is stirred at room temperature for a further 6 hours. The reaction solution is evaporated to dryness, suspended in ethyl acetate/hexane 1:1 and filtered, and the product is precipitated as a pale-yellow solid by addition of hexane ($\lambda$max=354 nm).

Example 5

Investigations of Photoisomerisation by Brief Irradiation

A 2% solution of the UV filter chromophore according to the invention or of the comparative compound in 1-propanol/Pelemol BIP (8/2) is applied to the rough side of a Plexiglas specimen slide (1 µl/cm$^2$). The sample is subsequently irradiated with solar-simulated UV light for 15 min (Atlas CPS+, setting 765 Wm$^{-2}$). The PMMA plates are then rinsed with 50 ml of isopropanol and measured in a UV/VIS spectrometer. The decrease in absorption at the absorption maximum is determined compared with the dark value.
Compounds Investigated:
A) (2,4-dimethoxycinnamoyl 6-O-ascorbate)
B) (3,4-dimethoxycinnamoyl 6-O-ascorbate) for comparison.
Result:
Compound A) exhibits a decrease in absorption of 26%, whereas compound B) has a decrease in absorption of 40%. The ortho-substituted cinnamic acid derivative thus exhibits a smaller decrease in absorption, and the result confirms the lesser formation of the cis isomer.

Example 6

Investigations of Photoisomerisation (Reversible Photoisomerisation) by Brief Irradiation A 2% solution of the UV filter chromophore according to the invention or of the comparative compound in 1-propanol/Pelemol BIP (8/2) is applied to the rough side of a Plexiglas specimen slide (1 µl/cm$^2$). The sample is subsequently irradiated with solar-simulated UV light for 15 min (Atlas CPS+, setting 765 Wm$^{-2}$). The PMMA plates are then rinsed with 50 ml of isopropanol and measured in a UV/VIS spectrometer. The decrease in absorption at the absorption maximum is determined compared with the dark value.
Compounds Investigated:
A) 2,4,6-trimethoxycinnamoyl 6-O-ascorbate
B) ethylhexyl 4-methoxycinnamate for comparison.
Result:
Compound A) exhibits a decrease in absorption of 20%, whereas compound B) has a decrease in absorption of 37%. The ortho-substituted cinnamic acid derivative thus exhibits a smaller decrease in absorption than the comparative component.

EXAMPLES OF PREPARATIONS

Example 1

General Formulation Notes

The described ascorbates of cinnamic acid derivatives can be incorporated both into the oil phase of preparations, such as, for example, emulsions, and into their water phase. Combined incorporation into the oil and water phases is preferably also possible, which enables synergy effects to arise with respect to the overall efficacy of the preparation. In particular in the case of incorporation into the water phase of cosmetic emulsions, a synergy effect can be achieved with respect to the overall UV protective action of the formulation between the water-soluble UV filter(s) and further oil-soluble UV filters present. For incorporation into the oil or water phase, it is advantageous to use solubility promoters. For example, the addition of alcohol components (e.g. ethanol, isopropanol) is advantageous here. The pH of the formulation should preferably be between pH=3 and pH=6 in order to achieve satisfactory stability of the ascorbate due to an acidic environment in the formulation. It is particularly preferred, for example, to buffer the pH of the water phase to pH=5 using citrate buffer, since this corresponds to the natural pH of the skin. In general, the ascorbates described can be incorporated into at least one lipophilic or hydrophilic phase of a preparation in such a way that either a clear solution is present or the substances are in dispersed form.

Example 2

W/O Emulsion—Numerical Data in % by Weight

|  | a | b | c | d | e |
|---|---|---|---|---|---|
| Cetyl PEG/PPG-10/1 dimethicone (Abil EM 90) | 3 | 3 | 3 | 3 | 3 |
| Polyglyceryl 4-isostearate (Isolan GI 34) | 1.5 | 1.5 | 1.5 | 1.5 | 1.5 |
| Butylphthalimide isopropylphthalimide (Pelemol ® BIP) | 5 | 5 | 5 | 5 | 5 |
| Dimethyl isosorbide (Arlasolve DMI) | 5 | 5 | 5 | 5 | 5 |
| 2,4-Dimethoxy-cinnamoyl 6-O-ascorbate | 2 | 1 | 0.5 | | |
| 2,4,6-Trimethoxy-cinnamoyl 6-O-ascorbate | | | | 1 | 1.5 |

-continued

|  | a | b | c | d | e |
|---|---|---|---|---|---|
| 2,3,4-Trimethoxy-cinnamoyl 6-O-ascorbate | 1 | 1.5 | 0.5 |  |  |
| 2,4,5-Trimethoxy-cinnamoyl 6-O-ascorbate |  |  |  | 1 | 1 |
| Uvinul ® A Plus (DHHB) |  | 1 | 1 | 1 |  |
| Ascorbic acid |  |  | 0.37 | 1 | 3 |
| Mineral Oil | 8 | 8 | 8 | 8 | 8 |
| Ethylhexyl stearate (Tegosoft ® OS) | 5 | 5 | 5 | 5 | 5 |
| Cyclomethicone (and) Aluminium/Magnesium Hydroxide Stearate (Gilugel SIL 5) | 5 | 5 | 5 | 5 | 5 |
| Preservative | 1 | 1 | 1 | 1 | 1 |
| Water | to 100 | to 100 | to 100 | to 100 | to 100 |
| 4-Methoxycinnamoyl 6-O-ascorbate | 1 | 2 | 3 | 4 | 5 |
| NaCl | 0.5 | 0.5 | 0.5 | 0.5 | 0.5 |
| EDTA | 0.1 | 0.1 | 0.1 | 0.1 | 0.1 |
| Citric acid q.s. |  |  |  |  |  |

Preparation:

Pelemol® BIP, Arlasolv DMI and emulsifiers are initially introduced. 2,4-Dimethoxycinnamoyl 6-O-ascorbate, 2,4,6-trimethoxycinnamoyl 6-O-ascorbate, 2,3,4-trimethoxycinnamoyl 6-O-ascorbate, 2,4,5-trimethoxycinnamoyl 6-O-ascorbate and Uvinul® A Plus are dissolved therein. The remaining constituents of the oil phase are added and mixed homogeneously. The water phase, adjusted to pH=4-5 using citric acid and comprising 4-methoxycinnamoyl 6-O-ascorbate, is emulsified in with stirring. The mixture is subsequently homogenised. The emulsions can be prepared under gentle conditions at room temperature. Cinnamoyl ascorbates present can be stabilised by increasing the content of ascorbic acid. The preparation is ideally carried out under an inert gas (exclusion of oxygen).

Example 3

Water-Resistant Sunscreen Spray—Numerical Data in % by Weight

| A |  |  |  |
|---|---|---|---|
| 2,4-Dimethoxycinnamoyl 6-O-ascorbate | 1 | 1 | 2 |
| 4-Methoxycinnamoyl 6-O-ascorbate | 0.5 | 0.5 | 0.5 |
| Diethylhexyl Syringylidenemalonate, Caprylic/Capric Triglyceride (Oxynex ® ST liquid) |  | 0.5 |  |
| 2-(4-Hydroxy-3,5-dimethoxybenzyl)malonic acid bis(2-ethylhexyl) ester RonaCare ® AP |  |  | 2 |
| Ascorbyl Palmitate |  |  | 1 |
| Cyprylic/capric Triglyceride (Miglyol 812 N) | 7 | 7 | 7 |
| Butylphthalimide isopropylphthalimide (Pelemol ® BIP) | 9 | 9 | 9 |
| C12-15 alkyl benzoate (Tegosoft ® TN) | 10 | 10 | 10 |
| Phenethyl benzoate (X-Tend 226) | 5 | 5 | 5 |
| RonaCare ® tocopherol acetate | 1 | 1 | 1 |

| B |  |  |  |
|---|---|---|---|
| Cyclopentasiloxane (Dow Corning 245) | 43.8 | 41.3 | 41.8 |
| 4-Methoxycinnamoyl 6-O-ascorbate | 0.5 | 0.5 | 0.5 |
| Phenyltrimethicone (Dow Corning 556) | 2 | 2 | 2 |
| Cyclopentasiloxane, dimethiconol Dow Corning 1501 Fluid | 20 | 20 | 20 |
| Perfume oil (q.s.) | 0.2 | 0.2 | 0.2 |

Preparation: the components of phase A are combined at room temperature and stirred until a clear solution or homogeneous dispersion is present. Phase B is subsequently mixed and added to phase B with stirring. Stirring is continued until finally the homogeneous product is present. The stability of the substances according to the invention can be increased by addition of antioxidants, such as Oxynex® ST liquid, RonaCare®AP or ascorbyl palmitate.

Example 4

Pump Hairspray—Numerical Data in % by Weight

| A |  |  |  |
|---|---|---|---|
| 2,4-Dimethoxycinnamoyl 6-O-ascorbate | 1 | 1 | 4 |
| 2,4,6-Trimethoxycinnamoyl 6-O-ascorbate | 1 |  |  |
| 2,3,4-Trimethoxycinnamoyl 6-O-ascorbate |  | 1 |  |
| 2,4,5-Trimethoxycinnamoyl 6-O-ascorbate |  |  | 1 |
| 4-Methoxycinnamoyl 6-O-ascorbate | 2 | 2 | 2 |
| Ethanol 96% extra pure | to 100 | to 100 | to 100 |
| PVP/VA copolymer PVP/VA W 735 | 6 | 6 | 6 |

| B |  |  |  |
|---|---|---|---|
| Diethylhexyl Syringylidenemalonate, Caprylic/Capric Triglyceride (Oxynex ® ST liquid) | 0.06 | 0.25 | 0.50 |
| PEG-75 lanolin BHT (Solan E-low dioxane) | 0.2 | 0.2 | 0.2 |
| Perfume (Frag 280853 Green Activating) | 0.1 | 0.1 | 0.1 |

| C |  |  |  |
|---|---|---|---|
| Water, demineralised | 13 | 13 | 13 |
| Titriplex III | 0.1 | 0.1 | 0.1 |
| PEG-12 dimethicone Dow Corning 193 fluid | 0.5 | 0.5 | 0.5 |
| 0.1% of D&C Red No 33 (CI 17200) in water | 0.2 | 0.2 | 0.2 |
| PEG-40 Hydrogenated Castor Oil (Cremophor RH 410) | 1 | 1 | 1 |

Preparation: pre-dissolve phase A until a clear solution is present. Add phase B to phase A with stirring. Pre-mix phase C and add to the remainder, stir until a homogeneous mixture has formed.

Example 5

W/O Emulsions—Numerical Data in % by Weight

| Emulsion | A | B | C | D | E | F |
|---|---|---|---|---|---|---|
| Polyglyceryl 2-dipolyhydroxystearate | 3 | 5 | 3 | | | |
| PEG-30 dipolyhydroxystearate | | | 2 | 3 | 4 | 5 |
| Sodium starch octenylsuccinate | 0.5 | 0.4 | | 0.3 | | 1 |
| Glycine | 0.3 | 0.3 | 0.5 | 0.4 | | |
| Alcohol | | 5 | 2 | 5 | 4 | |
| Magnesium sulfate | 0.2 | 0.3 | 0.3 | 0.4 | 0.5 | 0.2 |
| $C_{12-15}$ alkyl benzoate | 5 | 3 | | | 5 | |
| $C_{12-13}$ alkyl tartrate | | | 2 | | | |
| Butylene glycol dicaprylate/dicaprate | 5 | | | | 3 | 3 |
| Dicaprylyl ether | | | | 2 | | |
| Mineral oil | | 4 | | 6 | | 8 |
| Octyldodecanol | 2 | | | | | |
| Dicaprylic caprate | | | 2 | | 2 | 2 |
| Cyclomethicone | 5 | | 5 | 10 | | |
| Dimethicone | | | | 5 | | |
| Isohexadecane | | 1 | | | | |
| Butylene glycol | 5 | 8 | | | 3 | |
| Propylene glykol | | | 1 | | 5 | 3 |
| Glycerine | 3 | 5 | 7 | 10 | 3 | 3 |
| C18-38 acid triglycerides | 0.5 | | 1 | | 1 | |

| Emulsion | A | B | C | D | E | F |
|---|---|---|---|---|---|---|
| Titanium dioxide | 5 | 6 | 4 | | | 4 |
| Zinc oxide | 5 | | | | | |
| Bisethylhexyloxyphenol-methoxyphenyltriazine | | 3 | 3 | 2 | | |
| Ethylhexyltriazone | | 4.5 | 3 | | 3 | |
| 2,4-Dimethoxycinnamoyl 6-O-ascorbate | 2 | 0.5 | 1 | 1 | 3 | 1.5 |
| 4-Methoxycinnamoyl 6-O-ascorbate | 0.5 | 1.5 | 1 | 2 | 0.5 | 1.5 |
| Diethylhexylbutamidotriazone | | | 1.5 | 4 | | |
| Butylmethoxydibenzoyl-methane | 2 | 3 | 4 | | 1 | 3 |
| Uvinul ® A Plus | | | | | 4 | 2 |
| Ethylhexyl methoxycinnamate | | | | | 7 | 5 |
| 2,4-Dimethoxycinnamoyl 6-O-ascorbate coupled to gelatine | 1.5 | 5.5 | | 8 | 4.5 | 7.5 |
| Benzotriazole coupled to gelatine | 4 | | 6 | | | |
| Taurine | 0.1 | | | 0.5 | 0.2 | |
| Vitamin E acetate | 0.2 | 02 | | 0.3 | 0.1 | 0.5 |
| $Na_2H_2EDTA$ | 0.1 | 0.1 | 0.2 | 0.2 | 0.2 | 0.5 |
| C8-C16 alkylpolyglycoside | 1 | | | | | |
| Perfume, preservatives | q.s. | q.s. | q.s | q.s | qs. | qs. |
| Dyes, etc. | q.s. | q.s. | q.s. | q.s | q.s. | q.s. |
| Sodium hydroxide | q.s. | q.s. | q.s. | q.s | q.s. | q.s. |
| Water | to 100.0 | to 100.0 | to 100.0 | to 100.0 | to 100.0 | to 100.0 |

Example 6

Hair-Care Formulation—Numerical Data in % by Weight

Content in g of component per 100 g of formulation

| Component | A | B | C | D | E | F |
|---|---|---|---|---|---|---|
| Disodium EDTA | 0.1 | 0.1 | 0.1 | 0.1 | 0.1 | 0.1 |
| Oxynex ®ST | 2 | 2 | 2 | 2 | 2 | 2 |
| 4-Dimethoxycinnamoyl 6-O-ascorbate | 0.1 | 0.25 | 0.5 | 1.5 | 2 | 4 |
| 2,4-Dimethoxycinnamoyl 6-O-ascorbate | 4 | 2 | 1.5 | 0.5 | 0.25 | 0.1 |
| 2,4,6-Trimethoxycinnamoyl 6-O-ascorbate | 0.5 | 1 | 1.5 | 2 | 2.5 | 3 |
| Hexamidine diisethionate | 0.1 | 0 | 0 | 0 | 0 | 0 |
| Tetrahydrocurcumin | 0 | 0.5 | 0 | 0 | 0 | 0 |
| Glycyrrhetinic acid | 0 | 0 | 0.3 | 0 | 0 | 0 |
| Thiotaine ®[1] | 0 | 0 | 0 | 5 | 0 | 0 |
| N-undecylenoyl-L-phenylalanine | 0 | 0 | 0 | 0 | 1 | 0 |
| N-acetylglucosamine | 0 | 0 | 0 | 0 | 0 | 2 |
| Niacinamide | 5 | 5 | 5 | 5 | 5 | 5 |
| Citric acid | 0.015 | 0 | 0 | 0 | 0 | 0 |
| Isohexadecane | 3 | 3 | 3 | 3 | 3 | 3 |
| Isopropyl isostearate | 1.33 | 1.33 | 1.33 | 1.33 | 1.33 | 1.33 |
| Isopropyl N-laurosylsarcosinate | 0 | 0 | 5 | 0 | 0 | 0 |
| Sucrose polycottonseedate | 0.67 | 0.67 | 0.67 | 0.67 | 0.67 | 0.67 |
| Polymethylsilsesquioxane | 0.25 | 0.25 | 0.25 | 0.25 | 0.25 | 0.25 |
| Cetearyl glucoside + cetearyl alcohol | 0.2 | 0.2 | 0.2 | 0.2 | 0.2 | 0.2 |
| Behenyl alcohol | 0.4 | 0.4 | 0.4 | 0.4 | 0.4 | 0.4 |
| Ethylparaben | 0.2 | 0.2 | 0.2 | 0.2 | 0.2 | 0.2 |
| Propylparaben | 0.1 | 0.1 | 0.1 | 0.1 | 0.1 | 0.1 |
| Cetyl alcohol | 0.32 | 0.32 | 0.32 | 0.32 | 0.32 | 0.32 |
| Stearyl alcohol | 0.48 | 0.48 | 0.48 | 0.48 | 0.48 | 0.48 |
| Tocopheryl acetate | 0.5 | 0.5 | 0.5 | 0.5 | 0.5 | 0.5 |
| PEG-100 stearate | 0.1 | 0.1 | 0.1 | 0.1 | 0.1 | 0.1 |
| Glycerine | 7 | 7 | 7 | 7 | 7 | 7 |
| Titanium dioxide | 0.604 | 0.604 | 0.604 | 0.604 | 0.604 | 0.604 |

Example 7

Hair-Care Formulation—Numerical Data in % by Weight

Content in g of component per 100 g of formulation

| Component | G | H | I |
|---|---|---|---|
| Disodium EDTA | 0.1 | 0.1 | 0.1 |
| Oxynex ® ST | 2 | 2 | 2 |
| 2,3,4-Trimethoxycinnamoyl 6-O-ascorbate | 0.5 | 3.5 | 1.5 |
| 4-Methoxycinnamoyl 6-O-ascorbate | 1.5 | 0.5 | 2 |
| Cetylpyridinium chloride | 0.2 | 0 | 0 |
| Pitera ® | 0 | 10 | 0 |
| Ascorbyl glycoside | 0 | 0 | 2 |
| Niacinamide | 3.5 | 5 | 4 |
| Polyquaternium 37 | 0 | 0 | 0 |
| Isohexadecane | 3 | 2.5 | 2 |
| Isopropyl isostearate | 1.33 | 1.33 | 1.33 |
| Sucrose polycottonseedate | 0.67 | 0.67 | 0.67 |
| Polymethylsilsesquioxane | 0.25 | 0.25 | 0.25 |
| Cetearyl glucoside + cetearyl alcohol | 0.2 | 0.2 | 0.2 |
| Behenyl alcohol | 0.4 | 0.4 | 0.4 |
| Ethylparaben | 0.2 | 0.2 | 0.2 |
| Propylparaben | 0.1 | 0.1 | 0.1 |
| Cetyl alcohol | 0.32 | 0.32 | 0.32 |
| Stearyl alcohol | 0.48 | 0.48 | 0.48 |
| Tocopheryl acetate | 0.5 | 0.5 | 0.5 |
| PEG-100 stearate | 0.1 | 0.1 | 0.1 |
| Glycerine | 7 | 7 | 7 |
| Titanium dioxide | 0.604 | 0.604 | 0.604 |
| Polyacrylamide + C13-14 isoparaffin + laureth-7 | 2 | 2 | 2 |
| Panthenol | 1 | 1 | 1 |
| Benzyl alcohol | 0.4 | 0.4 | 0.4 |
| Dimethicone + dimethiconol | 2 | 2 | 2 |
| Water (to 100 g) | to 100 | to 100 | to 100 |
| TOTAL | 100 | 100 | 100 |

Example 8

O/W Emulsions—Numerical Data in % by Weight

| Emulsion | A | B | C | D | E | F |
|---|---|---|---|---|---|---|
| Glyceryl stearate citrate | 2.5 | 2 | 3 | | | |
| Sorbitan stearate | 0.5 | | | 2 | 1.5 | 2 |
| Polyglyceryl-3 methylglycose distearate | | | | 2.5 | 3 | 3 |
| Polyglyceryl-2 dipolyhydroxystearate | | 0.8 | | | | 0.5 |
| Cetearyl alcohol | | | | 1 | | |
| Stearyl alcohol | 2 | | | | | 2 |
| Cetyl alcohol | | 1 | | | 3 | |
| Acrylates/C$_{10-30}$ alkyl acrylate crosspolymer | | | 0.2 | | | 0.1 |
| Carbomer | | 0.2 | 0.3 | 0.2 | | |
| Xanthan gum | 0.4 | | 0.2 | 0.2 | 0.3 | 0.4 |
| C$_{12-15}$ alkyl benzoate | 5 | 3 | | | 5 | |
| C$_{12-13}$ alkyl tartrate | | 2 | | | | |
| Butylene glycol dicaprylat/dicaprat | 5 | | | | 3 | 3 |
| Dicaprylyl ether | | | | | 2 | |
| Octyldodecanol | 2 | | | | | |
| Dicapryl caprate | | 2 | | | 2 | 2 |
| Cyclomethicone | 5 | | 5 | 10 | | |
| Dimethicone | | | | 5 | | |
| Isohexadecane | | 1 | | | | |
| Butylene glycol | 5 | 8 | | | | 3 |
| Propylene gycol | | | 1 | | 5 | 3 |
| Glycerine | 3 | 5 | 7 | 10 | 3 | 3 |
| C18-C38 acid triglyceride | 0.5 | | 1 | | 1 | |
| Titanium dioxide | 5 | | | 2 | | |
| 2.2′-Methylenebis(6-(2H-benzotriazol-2-yl)-(1,1,3,3-tetramethylbutyl)phenol) | 2.5 | | | | | |
| 2.4,6-Tris(biphenyl)-1,3,5-triazine | | 2 | | | | |
| Merocyanine coupled to gelatine | 6 | | 6 | | 10 | 3 |
| Benzotriazole coupled to gelatine | | 5 | | 10 | | 3 |
| C8-C16 alkylpolyglycoside | 1 | 0.6 | | | | |
| UVASorb ® K2A | | | 2 | | | |
| Uvinul ® A Plus | 2 | | | | | 1 |
| Homosalate | | 5 | | 1 | | |
| Phenylbenzimidazole-sulfonic acid | | | 2 | | | 1 |
| Benzophenone-3 | 2 | | | | 2 | |
| Octyl salicylate | 5 | 5 | | 2 | | |
| Octocrylene | 2 | | | | 3 | 1 |
| 2,4-Dimethoxycinnamoyl 6-O-ascorbate | 1.0 | 2.0 | 0.25 | 1.0 | 2.0 | 0.5 |
| 4-Methoxycinnamoyl 6-O-ascorbate | 1.0 | 2.0 | 0.25 | 1.0 | 1.5 | 3.0 |
| Bisethylhexyloxyphenol-methoxyphenyltriazine | | 3 | 2 | 1 | | |
| Parsol ® SLX | | | | 3 | | |
| Dihydroxy acetate | | | | | 4 | |
| Taurine | 0.1 | | | | 0.5 | 0.2 |
| 8-Hexadecene-1,16-dicarboxylic acid | | 0.2 | | | | |
| Vitamin E acetate | 0.2 | 0.2 | | 0.3 | 0.1 | 0.5 |
| Na$_2$H$_2$EDTA | 0.1 | 0.1 | 0.2 | 0.2 | 0.2 | 0.5 |
| Perfume, preservatives | q.s. | q.s. | q.s. | q.s. | q.s. | q.s. |
| Dyes, etc. | q.s. | q.s. | q.s. | q.s. | q.s. | q.s. |
| Sodium hydroxide | q.s. | q.s. | q.s. | q.s. | q.s. | q.s. |
| Water | to 100.0 | to 100.0 | to 100.0 | to 100.0 | to 100.0 | to 100.0 |

Example 9

O/W Emulsions—Numerical Data in % by Weight

| Emulsion | G | H | I | K | L | M |
|---|---|---|---|---|---|---|
| Ceteareth-20 | 1 | 1.5 | 1 | | | |
| Sorbitan stearate | | | 0.5 | | 0.5 | |
| Glyceryl stearate SE | | | | 1 | 1 | 1.5 |
| Emulgade F ® | | | | 2.5 | 2.5 | 3 |
| Cetearyl alcohol | | | | 1 | | |
| Stearyl alcohol | | | | | 1.5 | |
| Cetyl alcohol | | | 0.5 | | | 2 |
| Acrylates/$C_{10-30}$ alkyl acrylate crosspolymer | 0.2 | 0.4 | 0.3 | 0.1 | | |
| Carbomer | | | | | 0.3 | |
| Xanthan gum | | | | 0.4 | | 0.4 |
| $C_{12-15}$ alkyl benzoate | 5 | 3 | | | 5 | |
| 2-Phenyl benzoate | | 2 | | | | |
| Butylene glycol dicaprylat/dicaprat | 5 | | | | 3 | 2 |
| Dicaprylyl ether | | | | | 2 | |
| Diethylhexyl naphthalate | 2 | | | | | |
| Dicapryl caprate | | 2 | | | 2 | 2 |
| Cyclomethicone | 5 | | 5 | 10 | | |
| Isohexadecane | | | | 5 | | |
| Mineral oil | | 1 | | | | |
| Propylene glycol | | | 4 | | | |
| Glycerine | 5 | 7 | 3 | 5 | 6 | 8 |
| C18-38 acid triglyceride | 0.5 | | 1 | | 1 | |
| Titanium dioxide | 5 | | 3 | 2 | | |
| NeoHeliopan ® AP | | 2 | | | 1 | 1 |
| Phenylbenzimidazolesulfonic acid | 1 | | | 1 | 2 | 1 |
| Ethylhexyl methoxycinnamate | 5 | | 4 | 4 | | |
| Ethylhexyltriazone | | 2 | | 1 | | |
| Diethylhexylbutamido-triazane | 1 | | | | | |
| Butylmethoxydibenzoyl-methane | 2.5 | | 2 | 2 | | 1 |
| Bisethylhexyloxyphenol-methoxyphenyltriazine | 2 | | | | | |
| 4-Methylbenzylidene-camphor | 3 | | | | | |
| Parsol ® SLX | | | | | 2 | |
| 2,3,4-Trimethoxycinnamoyl 6-O-ascorbate | 0.5 | 1.0 | 2.0 | 0.25 | 0.75 | 1.5 |
| 2,4,6-Trimethoxycinnamoyl 6-O-ascorbate | 0.5 | 1.0 | 2.0 | 0.25 | 0.75 | 1.5 |
| 4-Methoxycinnamoyl 6-O-ascorbate | 0.5 | 1.0 | 2.0 | 1.5 | 1.5 | 3.0 |
| Creatinin | 0.1 | 0.01 | 0.05 | | | |
| Creatin | 0.5 | 0.2 | 0.1 | | | |
| Licorice extract/licochalcone | | | | 0.5 | | |
| Vitamin E acetate | 0.2 | | | 0.5 | 0.5 | 0.5 |
| Tapioca starch | | 3 | | | 2 | |
| $Na_2H_2EDTA$ | 0.1 | | 0.2 | | | 0.5 |
| Perfume, preservatives | q.s. | q.s. | q.s. | q.s. | q.s. | q.s. |
| Dyes, etc. | q.s. | q.s. | q.s. | q.s. | q.s. | q.s. |
| Sodium hydroxide | q.s. | q.s. | q.s. | q.s. | q.s. | q.s. |
| Water | to 100.0 | to 100.0 | to 100.0 | to 100.0 | to 100.0 | to 100.0 |

Example 10

O/W Emulsions—Numerical Data in % by Weight

| Emulsion | N | O | P | Q | R | S |
|---|---|---|---|---|---|---|
| Glyceryl stearate SE | | 2 | | 2 | | |
| Glyceryl stearate | 2 | | 2 | | | |
| PEG-40 stearate | | | 2 | | 1 | |

-continued

| Emulsion | N | O | P | Q | R | S |
|---|---|---|---|---|---|---|
| PEG-10 stearate | | | | 2.5 | 1 | |
| Ceteareth-20 | | | | | | 2.6 |
| Sodium cetyl phosphate | | | | | 2 | |
| Glyceryl stearate, ceteareth-12, ceteareth-20, cetearyl alcohol, cetyl palmitate | | | | | | 5.4 |
| Stearic acid | 3 | 2 | | | 2 | |
| Stearyl alcohol | | 2 | 2 | | | |
| Stearyl alcohol | 0.5 | | 2 | | | |
| Cetyl alcohol | 3 | | | 2 | | |
| Acrylates/C$_{10-30}$ alkyl acrylate crosspolymer | | | 0.2 | | 0.4 | |
| Carbomer | | 0.3 | | 0.3 | 0.3 | |
| Xanthan gum | | 0.3 | 0.4 | | | |
| C$_{12-15}$ alkyl benzoate | 5 | | | | 5 | 3 |
| 2-Phenyl benzoate | 5 | | | | | |
| Butylene glycol dicaprylate/dicaprate | | 5 | | 4 | | 3 |
| Dicaprylyl ether | | 2 | | | 3 | |
| Diethylhexyl naphthalate | 3 | | | | | |
| Cyclomethicone | 2 | | 10 | 2 | | |
| Isohexadecane | | | | 2 | 3 | |
| Mineral oil | | | | | 3 | |
| Propanediol | | 3 | | 5 | | |
| Glycerine | 3 | 5 | 10 | 7 | 4 | 5 |
| Titanium dioxide | 2 | 4 | | | | |
| Zinc oxide | | | | | 2 | |
| Drometrizole trisiloxane | | | | | 3 | |
| Ethylhexyl methoxycinnamate | | 6 | 5 | | | |
| Phenylbenzimidazolesulfonic acid | | 0.5 | 2 | | 1 | |
| Homosalate | 5 | | | 7 | | |
| Butylmethoxydibenzoyl-methane | | 3 | | | | |
| Bisethylhexyloxyphenol-methoxyphenyltriazine | | 2 | 3 | | | |
| Octyl salicylate | | | | 5 | | |
| Octocrylene | | | | | 3 | |
| 2,4,5-Trimethoxycinnamoyl 6-O-ascorbate | 0.25 | 1.5 | 0.5 | 2.5 | 1.0 | 3.0 |
| 4-Methoxycinnamoyl 6-O-ascorbate | 0.5 | 1.0 | 1.5 | 2.5 | 3.0 | 3.0 |
| Parsol ® SLX | 4 | | | | | 5 |
| PVP hexadecene copolymer | 0.5 | | 1 | | 0.8 | |
| Coenzyme Q 10 | 0.2 | 0.02 | | 0.3 | | |
| Vitamin E acetate | 0.2 | | 0.3 | | 0.8 | 0.5 |
| Na$_2$H$_2$EDTA | 0.1 | | | | | 0.5 |
| Perfume, preservatives | q.s. | q.s. | q.s. | q.s. | q.s. | q.s. |
| Dyes, etc. | q.s. | q.s. | q.s. | q.s. | q.s. | q.s. |
| Sodium hydroxide | q.s. | q.s. | q.s. | q.s. | q.s. | q.s. |
| Water | to 100.0 | to 100.0 | to 100.0 | to 100.0 | to 100.0 | to 100.0 |

Example 11

Hydrodisperions (Lotions and Sprays)—Numerical Data in % by Weight

| | A | B | C | D | E | F |
|---|---|---|---|---|---|---|
| Glyceryl stearate citrate | | 0.4 | | | | |
| Cetyl alcohol | | | | | 2 | |
| Sodium carbomer | | | | | 0.3 | |
| Acrylates/C$_{10-30}$ alkyl acrylate crosspolymer | 0.3 | | 0.3 | 0.4 | 0.1 | 0.1 |
| Cetsareth-20 | | | 1 | | | |
| Xanthan gum | | | | 0.15 | | 0.5 |
| Dimethicone/vinyl-dimethicone crosspolymer | | | | 5 | | 3 |
| UVASorb ® K2A | | | | | 3.5 | |
| Uvinul ®A Plus | 0.25 | | 0.5 | | 2 | 1.5 |

-continued

|  | A | B | C | D | E | F |
|---|---|---|---|---|---|---|
| Butylmethoxydibenzoyl-methane | 1.2 |  | 3.5 |  |  |  |
| Bisethylhexyloxyphenol-methoxyphenyltriazine | 2 | 2 |  | 0.25 |  |  |
| Terephthalidenedicamphor-sulfonic acid |  |  |  |  |  | 0.5 |
| Disodium phenyl-dibenzimidazole tetrasulfonate |  |  |  |  |  | 1 |
| Phenylbenzimidazole-sulfonic acid |  |  | 2 |  |  |  |
| Ethylhexyl methoxycinnamate | 5 |  | 7 |  | 5 | 8 |
| Diethylhexylbutamido-triazone |  |  | 2 | 2 |  |  |
| Ethylhexyltriazone | 4 | 3 |  |  | 4 |  |
| Octocrylene |  |  |  | 10 |  | 2.5 |
| 2,4-Dimethoxycinnamoyl 6-O-ascorbate | 0.25 | 1.5 | 0.5 | 2.5 | 1 | 5 |
| 4-Methoxycinnamoyl 6-O-ascorbate | 1 | 2 | 1 | 2 | 1 | 2 |
| C$_{12-15}$ alkyl benzoate | 2 |  | 2.5 |  |  |  |
| Phenethyl benzoate | 4 |  |  | 7.5 |  | 5 |
| C$_{18-36}$ triglyceride fatty acid |  |  | 1 |  |  |  |
| Butylene glycol dicaprylat/dicaprate |  |  |  |  | 6 |  |
| Dicaprylyl carbonate |  | 3 |  |  |  |  |
| Dicaprylyl ether |  | 2 |  |  |  |  |
| Cyclomethicone |  |  |  | 1.5 |  |  |
| Lanolin |  |  |  |  | 0.35 |  |
| PVP hexadecene copolymer | 0.5 |  | 0.5 |  | 0.5 | 1 |
| Ethylhexyloxyglycerine |  | 0.75 |  | 1 |  | 0.5 |
| Glycerine | 10 | 5 | 5 |  | 5 | 15 |
| Butylene glycol |  | 7 |  |  |  |  |
| *Glycine* soya |  |  |  | 1 |  |  |
| Vitamin E acetate | 0.5 | 0.25 | 05 | 0.25 | 0.75 | 1 |
| α-Glycosylrutin |  |  |  |  | 0.25 |  |
| Trisodium EDTA |  | 1 | 1 | 0.1 | 0.2 |  |
| Idopropynyl butylcarbamate | 0.2 | 0.1 |  |  |  | 0.15 |
| Methylparaben | 0.5 |  | 0.2 |  | 0.15 |  |
| Phenoxyethanol | 0.5 | 0.4 | 0.4 |  | 1 | 0.6 |
| Ethanol | 3 | 10 | 4 | 3.5 |  | 1 |
| Perume, dyes | q.s. | q.s. | q.s. | qs. | q.s. | q.s. |
| Water | to 100 | to 100 | to 100 | to 100 | to 100 | to 100 |
| Neutralisers (sodium hydroxide, potassium hydroxid) | qs | qs | qs | qs | qs | qs |

Example 12

Aqueous and Aqueous/Alcoholic Formulations—Numerical Data in % by Weight

|  | A | E | C | D | E | F |
|---|---|---|---|---|---|---|
| Ethanol | 50 | 5 | 2 | 40 | 15 |  |
| Hydroxyethylcellulose | 0.5 |  |  |  |  |  |
| Acrylates/C10-30 alkyl acrylate crosspolymer |  |  |  | 0.3 | 0.6 |  |
| Cocoatnidopropylbetain |  |  | 0.3 |  |  |  |
| UVASorb ® K2A |  |  |  |  | 2 |  |
| Uvinul ® A Plus | 5 |  |  |  |  |  |
| Butylmethoxydibenzoylmethane | 0.5 |  |  | 3 |  |  |
| Disodium phenyldibenzimid-azoletetrasulfonate |  | 2 | 1 |  |  |  |
| Phenylbenzimidazolesulfonic acid |  | 5 | 3 |  | 2 | 4 |
| Ethylhexyl methoxycinnamate | 10 |  |  |  | 3 |  |
| Diethylhexylbutamidotriazone |  |  |  | 3 |  |  |
| Ethylhexyltriazone |  |  |  |  | 2 |  |

|  | A | E | C | D | E | F |
|---|---|---|---|---|---|---|
| Octocrylene |  |  |  | 5 |  |  |
| 4-Methoxycinnamoyl 6-O-ascorbate | 2.5 | 0.75 | 1.5 | 3 | 3.5 | 4 |
| 2,4,6-Trimethoxycinnamoyl 6-O-ascorbate | 0.25 | 0.50 | 0.75 | 1 | 1.25 | 1.5 |
| $C_{12-15}$ alkyl benzoate |  |  |  | 3 |  |  |
| C18-36 triglyceride fatty acid |  |  |  | 1 |  |  |
| Butylene glycol dicaprylate/dicaprate | 2 |  |  |  |  |  |
| C12-13 alkyl tartrate |  |  |  |  | 5 |  |
| Cyclomethicone | 4 |  |  | 2 |  |  |
| Insect repellent ® 3535 |  |  |  | 5 |  |  |
| Dimethicone |  |  |  |  | 3 |  |
| PVP hexadecene copolymer |  | 0.5 |  | 1 |  | 0.5 |
| Ethylhexyloxyglycerine |  | 0.5 |  |  |  |  |
| Glycerine | 5 | 7 | 3 | 8 |  | S |
| Butylene glycol |  |  | 5 |  | 5 |  |
| Metylpropanediol |  |  |  | 4 |  |  |
| Vitamin E acetate |  | 0.3 | 0.2 | 0.5 |  |  |
| Panthenol | 0.5 |  | 0.2 |  |  | 0.3 |
| Creatinin |  |  | 0.01 |  | 0.02 |  |
| Creatin |  |  | 0.1 |  | 0.2 |  |
| PEG-40 hydrogenated castor oil |  | 0.5 | 0.3 |  |  | 0.5 |
| Trisodium EDTA | 0.3 | 0.2 | 0.2 | 0.2 | 0.2 | 0.5 |
| Preservatives | q.s. | q.s. | q.s. | q.s. | q.s. | q.s. |
| Sodium hydroxide | q.s. | q.s. | q.s. | q.s. | q.s. | q.s. |
| Perfume, dyes | q.s. | q.s. | q.s. | q.s. | q.s. | q.s. |
| Water | to 100 | to 100 | to 100 | to 100 | to 100 | to 100 |

Example 13

Cosmetic Foams—Numerical Data in % by Weight

| Emulsion | A | B | C |
|---|---|---|---|
| Stearic acid | 2 | 2 |  |
| Palmitic acid |  |  | 1.5 |
| Cetyl alcohol | 2.5 | 2 |  |
| Stearyl alcohol |  |  | 3 |
| PEG-100 stearate |  |  | 3.5 |
| PEG-40 stearate |  | 2 |  |
| PEG-20 stearate | 3 |  |  |
| Sorbitan stearate |  | 0.8 |  |
| $C_{12-15}$ alkyl benzoate | 5 |  |  |
| $C_{12-13}$ alkyl tartrate |  |  | 7 |
| Butylene glycol dicaprylate/dicaprate |  | 6 |  |
| Dicaprylyl ether |  |  | 2 |
| Cyclomethicone |  | 2 | 3 |
| Butylene glycol | 1 |  |  |
| Isohexadecane | 2 |  |  |
| Methylpropanediol |  |  |  |
| Propylene glycol |  |  | 5 |
| Glycerine | 5 | 7 |  |
| UVASorb ® K2A |  |  | 2 |
| Uvinul ® A Plus | 2 | 3 |  |
| 2,4-Dimethoxycinnamoyl 6-O-ascorbate | 0.5 | 1 | 1.5 |
| 4-Methoxycinnamoyl 6-O-ascorbate | 1.5 | 1 | 0.5 |
| Parsol SLX ® |  | 3 |  |
| Homosalate |  | 5 |  |
| Phenylbenzimidazolesulfonic acid |  | 2 | 2 |
| Benzophenone-3 | 2 |  |  |
| Octylsalicylate |  |  | 5 |
| Octocrylene | 2 |  |  |

| Emulsion | A | B | C |
|---|---|---|---|
| Bisethylhexyloxyphenol-methoxyphenyltriazine |  | 3 |  |
| 2.2'-Methylenebis(6-(2H-benzotriazol-2-yl)-4-(1,1,3,3-tetramethylbutyl)phenol) |  |  | 8 |
| 2,4,6-Tris(biphenyl)-1,3,5-triazine | 5 |  | 4 |
| C8-C16 alkylpolyglycoside | 1 |  |  |
| Vitamin E acetate | 0.6 | 0.5 | 0.2 |
| Creatin/creatinin |  |  | 0.5 |
| BHT |  |  | 0.1 |
| $Na_2H_2EDTA$ | 0.50 |  |  |
| Perfume, preservatives | q.s. | q.s. | q.s. |
| Dyes, etc. | q.s. | q.s. | q.s. |
| Sodium hydroxide | q.s. |  | q.s. |
| Potassium hydroxide |  | q.s. |  |
| Water | to 100.0 | to 100.0 | to 100.0 |

Example 14

Cosmetic Foams—Numerical Data in % by Weight

| Emulsion | D | E | F | G |
|---|---|---|---|---|
| Stearic acid | 2 |  |  |  |
| Palmitic acid |  |  | 3 | 3 |
| Cetyl alcohol |  | 2 |  |  |
| Cetylstearyl alcohol |  |  | 2 | 2 |
| Stearyl alcohol |  |  |  |  |
| PEG-100 stearate |  | 4 |  |  |
| PEG-40 stearate | 2 |  |  |  |
| PEG-20 stearate |  |  | 3 | 3 |
| Sorbitan stearate | 0.8 |  |  |  |
| Tridecyl trimellitate |  | 5 |  |  |
| $C_{12-15}$ alkyl benzoate |  |  | 3 | 3 |

-continued

| Emulsion | D | E | F | G |
|---|---|---|---|---|
| Butylene glycol dicaprylate/dicaprate | 8 | | | |
| Octyldodecanol | | 2 | | |
| Cocoglyceride | | | | 2 |
| Dicaprylyl ether | | | 2 | 2 |
| Cyclomethicone | | | | |
| Dimethicone | 1 | | 2 | 2 |
| Isohexadecane | | 3 | | |
| Methylpropanediol | | 4 | | |
| Propylene glycol | | | | |
| Glycerine | 5 | | 6 | 6 |
| NeoHeliopan ® AP | | 2 | | |
| Phenylbenzimidazolesulfonic acid | 1 | | | 1 |
| 2,4,6-Trimethoxycinnamoyl 6-O-ascorbate | 0.75 | 1.5 | 3.0 | 6.0 |
| 4-Methoxycinnamoyl 6-O-ascorbate | 6 | 3 | 1.5 | 0.75 |
| Ethylhexyl methoxycinnamate | 5 | | 4 | 4 |
| Ethylhexyltriazone | | 2 | | 1 |
| Eusolex T-AVO ® | 2 | | | |
| Diethylhexylbutamidotriazone | 1 | | | |
| Butylmethoxydibenzoyl-methane | 2.5 | | 2 | 2 |
| Bisethylhexyloxyphenol-methoxyphenyltriazine | 2 | | | |
| Vitamin E acetate | 0.2 | | 0.3 | 0.3 |
| Na₂H₂EDTA | | | | |
| Perfume, preservatives Dyes, etc. | | | | |
| Sodium hydroxide | | q.s. | q.s. | |
| Triethanolamine | q.s. | | | q.s. |
| Water | to 100.0 | to 100.0 | to 100.0 | to 100.0 |

Example 15

Sunscreen Lotions (O/W)—Numerical Data in % by Weight

| Emulsion | A | B | C | D | E | F |
|---|---|---|---|---|---|---|
| A | | | | | | |
| Octocrylene | 1.5 | 2 | | | | |
| Polycrylene | | | 3 | 3 | | |
| Bisethylhexyl hydroxy-dimethoxybenzylmalonate (RonaCare AP) | 1.5 | | 1 | 1 | 1.5 | 1 |
| Bisethylhexyl hydroxy-dimethoxybenzylidene-malonate (Oxynex ST) | | 1 | | | 1.5 | |
| 1-(4-tert-Butylphenyl)-3-(4-methoxyphenyl)propane-1,3-dione (Eusolex 9020) | | | | | | 2 |
| 2,4-Dimethoxycinnamoyl 6-O-ascorbate | 2 | | | 1 | 0.5 | 1.5 |
| 4-Methoxycinnamoyl 6-O-ascorbate | | 2 | 1 | | 1.5 | 0.5 |
| C12-15 alkyl benzoate | 2 | | | 2 | 1 | 2 |
| Dioctyl adipate | 1 | 1 | | 3 | | |
| Dimethicone | 1 | 1 | | | 1 | |
| Isopropyl alcohol | 3 | 3 | 3 | 3 | 3 | 3 |
| Cocoglycerides (e.g. Myritol 331) | 4 | 5 | 6 | 3.5 | 8 | |
| Capric/caprylic triglyceride (e.g. Mygliol 812) | 4 | 5 | 6 | 3.5 | 2 | 10 |
| Glyceryl stearate, cetyl alcohol, PEG-75 stearate, ceteth-20, steareth-20 | 3.3 | 3.3 | 3.3 | 3.3 | 3.3 | 3.3 |
| PPG-1-PEG-9 lauryl glycol ether | 0.5 | 0.5 | 0.5 | 0.5 | 0.5 | 0.5 |

-continued

| Emulsion | A | B | C | D | E | F |
|---|---|---|---|---|---|---|
| Diisostearoyl trimethylolpropane siloxy silicate | 1.5 | 1.5 | 1.5 | 1.5 | 1.5 | 1.5 |
| B | | | | | | |
| Ectoin | 0.1 | 0.1 | 0.1 | 0.1 | 0.1 | 0.1 |
| Allantoin | 0.2 | 0.2 | 0.2 | 0.2 | 0.2 | 0.2 |
| Dimethicone copolyol phosphate | 2.5 | 2.5 | 2.5 | 2.5 | 2.5 | 2.5 |
| Butylene glycol | 2.5 | 2.5 | 2.5 | 2.5 | 2.5 | 2.5 |
| Water | to 100 | to 100 | to 100 | to 100 | to 100 | to 100 |
| C | | | | | | |
| PPG-1 trideceth-6, polyquaternium-37, propylene glycol dicaprylate/dicaprate | 0.5 | 1 | | | | |
| D | | | | | | |
| Propylene glycol, DMMDM hydantoin, ethylparaben | 0.7 | 5 | 7 | 10 | 3 | 3 |
| Perfume | 0.3 | 1 | | 1 | | |

Preparation:

Firstly, the substances according to the invention are pre-dissolved or predispersed in isopropanol (alternatively ethanol). If necessary, further or alternative alcohols and glycols are employed, such as, for example, ethanol, glycerol or decyl alcohol. This pre-solution is added to the other components of phase A. Phase A is subsequently heated to 50-60° C. Then heat phase B to 60° C., then disperse in phase C with stirring. Stir phase A into phase B/C with vigorous stirring. Cool with stirring, and add phase D at 40° C. Homogenise, and cool to 25° C. with stirring. Note: the pre-solution described can alternatively also be added to the finished emulsion at room temperature with stirring. Since substances according to the invention contain oxidation-sensitive groups, it is advisable to formulate or produce under the most inert conditions possible.

Example 16

Hair Dye Comprising Various Components

Component A:

Tocopherol, Linalool, Geraniol, Disodium EDTA, Perfume, Toluene-2,5-Diamine Sulfate, Ascorbic Acid, Alcohol Denat., Sodium Sulfite, Sodium Hydroxide, Sodium Cocoyl Isethionate, Bis-Ethylhexyl Hydroxydimethoxy Benzylmalonate, 2-Methylresorcinol, 6-Amino-m-Cresol, 4-Amino-2-Hydroxytoluene, 4-Amino-m-Cresol, Sodium Lauryl Sulfate, Ammonia, Lanolin Alcohol, Glycol Distearate, Sodium Laureth Sulfate, Glyceryl Stearate, Cetearyl Alcohol, Aqua.

Component B:

Aqua, Hydrogen Peroxide, Cetearyl Alcohol, PPG-38-Buteth-37, Petrolatum, Laureth-2, Sodium Cetearyl Sulfate, Salicylic Acid, Disodium Phosphate, Phosphoric Acid, Etidronic Acid.

Component C:

Ethanolic solution of 2,4-dimethoxycinnamoyl 6-O-ascorbate (2% by weight) additionally comprising 4-methoxycinnamoyl 6-O-ascorbate (2% by weight) and bisethylhexyl hydroxydimethoxy benzylmalonate (1% by weight).

Use:

For colouring hair, the following sequence is preferably followed: firstly, the hair is pre-treated with component C, components B and C are subsequently mixed and applied to the hair.

A further application variant proposes integrating 2,4-dimethoxycinnamoyl 6-O-ascorbate and 4-methoxycinnamoyl 6-O-ascorbate directly into component A.

The invention claimed is:

1. A compound of the formula I

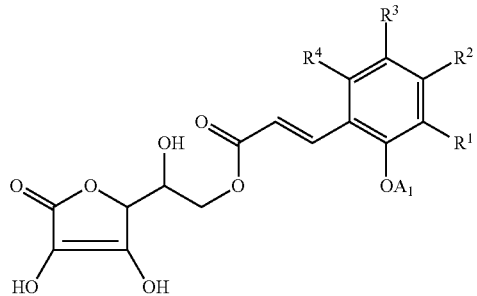

where
- $A_1$ stands for H or a straight-chain or branched alkyl group having 1 to 20 C atoms, R1 to R4 each stand, independently of one another, for H, straight-chain or branched alkoxy groups having 1 to 20 C atoms, hydroxyl, fluorinated straight-chain or branched alkoxy groups having 1 to 20 C atoms or alkylcarbonyloxy, and alkylcarbonyloxy stands for alkyl-C(=O)—O, where alkyl denotes a straight-chain or branched alkyl group having 1 to 10 C atoms.

2. The compound according to claim 1, wherein $A_1$ denotes a straight-chain or branched alkyl group having 1 to 4 C atoms.

3. The compound according to claim 1, wherein the substituent $R^2$ denotes hydroxyl or a straight-chain or branched alkoxy group having 1 to 4 C atoms.

4. The compound according to claim 1, wherein at least one further substituent selected from $R^1$, $R^3$ or $R^4$ stands for hydroxyl or a straight-chain or branched alkoxy group having 1 to 20 C atoms.

5. A process for the preparation of the compound of claim 1, comprising esterifying ascorbic acid with a compound of the formula II,

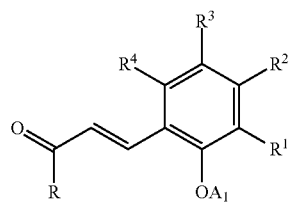

where R denotes OH, halogen or an active ester, halogen denotes Cl, Br or I, and the substituents $A_1$, $R^1$ to $R^4$ have a meaning indicated in claim 1.

6. A composition comprising at least one compound according to claim 1 and at least one carrier.

7. The composition according to claim 6, wherein the at least one compound of claim 1 is present in an amount of 0.05 to 10% by weight.

8. The composition according to claim 6, further comprising an organic UV filter.

9. The composition according to claim 6, further comprising an inorganic UV filter.

10. The composition according to claim 6, further comprising an ascorbic acid derivative.

11. The composition according to claim 6, further comprising at least one cosmetic active compound, selected from antioxidants, anti-aging active compounds, anti-cellulite active compounds, self-tanning substances, skin-lightening active compounds or vitamins.

12. A process for preparing a composition comprising mixing at least one compound of claim 1 with a carrier or assistants.

13. A method comprising applying a compound of claim 1 to skin and/or hair.

14. The composition according to claim 10, wherein the at least one further ascorbic acid derivative is ascorbic acid, magnesium ascorbyl phosphate or ascorbyl palmitate.

* * * * *